(12) United States Patent
Garcia-Lopez et al.

(10) Patent No.: US 8,232,307 B2
(45) Date of Patent: Jul. 31, 2012

(54) INDANE-AMINE DERIVATIVES, THEIR PREPARATION AND USE AS MEDICAMENTS

(75) Inventors: Monica Garcia-Lopez, Barcelona (ES); Antonio Torrens-Jover, Terrassa (ES)

(73) Assignee: Laboratorios del Dr. Esteve, S.A., Barcelona (ES)

( * ) Notice: Subject to any disclaimer, the term of this patent is extended or adjusted under 35 U.S.C. 154(b) by 134 days.

(21) Appl. No.: 12/667,587

(22) PCT Filed: Jul. 4, 2008

(86) PCT No.: PCT/EP2008/005500
§ 371 (c)(1),
(2), (4) Date: Mar. 12, 2010

(87) PCT Pub. No.: WO2009/003719
PCT Pub. Date: Jan. 8, 2009

(65) Prior Publication Data
US 2011/0053980 A1    Mar. 3, 2011

(30) Foreign Application Priority Data
Jul. 5, 2007 (EP) .................................. 07384028

(51) Int. Cl.
*A61K 31/415* (2006.01)
*C07D 231/00* (2006.01)
(52) U.S. Cl. ..................................... 514/403; 548/356.1
(58) Field of Classification Search ................. 514/403; 548/356.1
See application file for complete search history.

(56) References Cited

U.S. PATENT DOCUMENTS

| 4,820,705 A * | 4/1989 | Nickl et al. ................... 514/247 |
| 7,799,782 B2 * | 9/2010 | Munson et al. ............. 514/234.5 |
| 8,097,641 B2 * | 1/2012 | Garcia-Lopez et al. ....... 514/406 |

FOREIGN PATENT DOCUMENTS

| WO | 95/18617 A | 7/1995 |
| WO | 96/34849 A | 11/1996 |
| WO | 2005/113527 A | 12/2005 |

OTHER PUBLICATIONS

Holmberg Paer et al; "Novel 2-Aminotetralin and 3-AminoChroman Derivatives as Selective Serotonin 5-HT7 Receptor Agonists and Antagonists," Journal of Medicinal Chemistry, American Chemical Society, 2004, pp. 3927-3930, vol. 47, No. 16, Washington, US.
Bogeso K P et al; "3-Phenyl-1-Indanamines. Potential Antidepressant Activity and Potent Inhibition of Dopamine, Norephinephrine, and Serotonin Uptake," Journal of Medicinal Chemistry, American Chemical Society, Dec. 1, 1985, pp. 1817-1828, vol. 28, No. 12, Washington, US.
International Search Report for PCT/EP2008/005500 dated Jun. 30, 2009.

* cited by examiner

*Primary Examiner* — Rei-tsang Shiao
(74) *Attorney, Agent, or Firm* — Heslin Rothenberg Farley & Mesiti P.C.

(57) ABSTRACT

The present invention relates to indane-amine compounds of general formula (I) and compositions thereof, methods for their preparation, and the use of said compounds for the treatment of humans or animals.

28 Claims, 2 Drawing Sheets

Figure 1. Ortep-Plot (50 %) with labeling scheme.
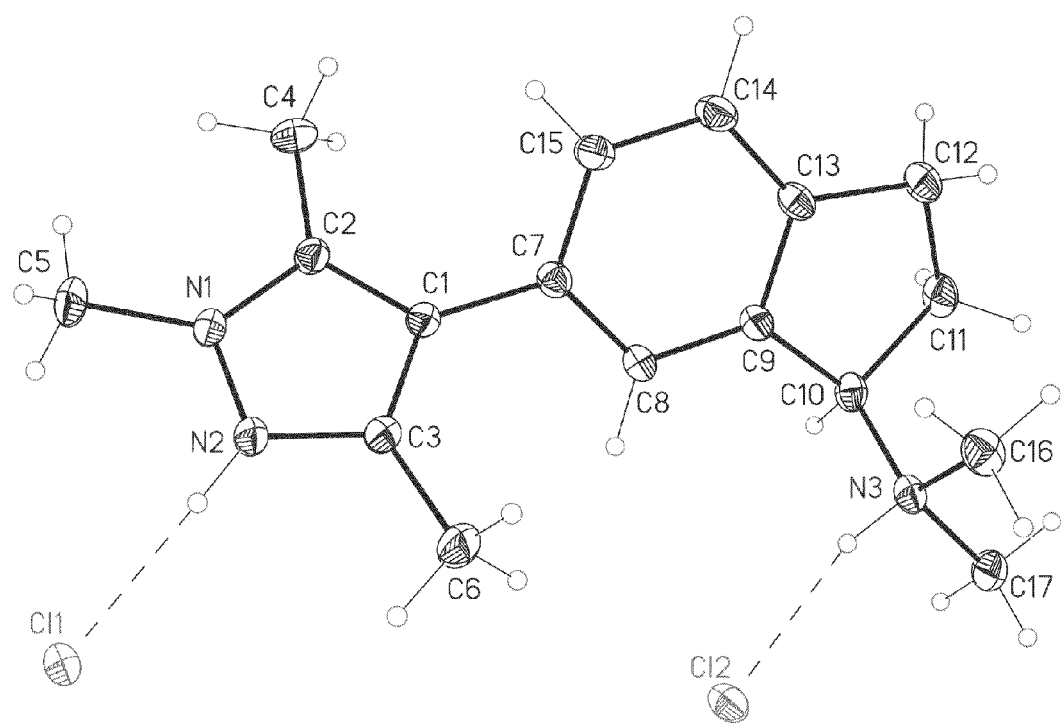

Figure 2. Ortep-Plot (50 %).
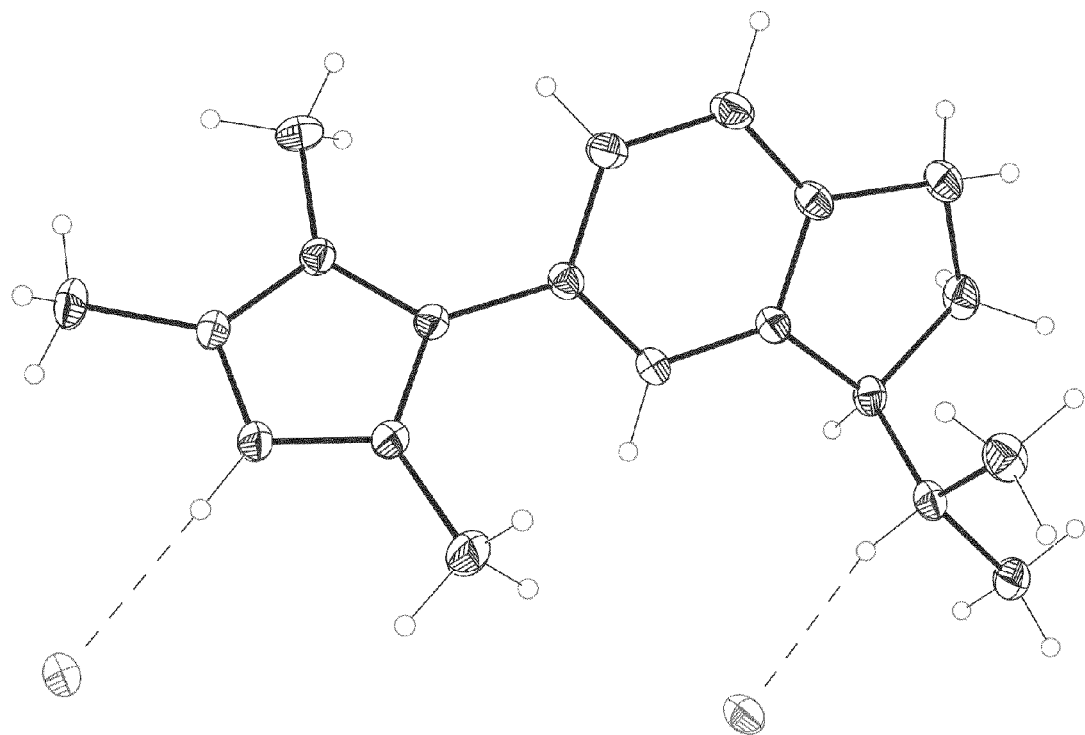

INDANE-AMINE DERIVATIVES, THEIR PREPARATION AND USE AS MEDICAMENTS

CROSS REFERENCE TO RELATED APPLICATIONS

This application is a U.S. National Phase filing under 35 U.S.C. §371 of International Application PCT/EP2008/005500, filed Jul. 4, 2008, and published as WO 2009/003719 on Jan. 8, 2009. PCT/EP2008/005500 claimed benefit of priority from European Patent Application No. EP 07384028.2, filed Jul. 5, 2007. The entire contents of each of the prior applications are incorporated herein by reference.

The present invention relates to indane-amine compounds of general formula (I), methods for their preparation, medicaments comprising these compounds as well as their use for the preparation of a medicament for the treatment of humans or animals The search for new therapeutic agents has been greatly aided in recent years by better understanding of the structure of proteins and other biomolecules associated with target diseases. One important class of proteins that has been the subject of extensive study is the family of 5-hydroxytryptamine (serotonin, 5-HT) receptors. The 5-HT$_7$ receptor discovered in 1993 belongs to this family and has attracted great interest as a valuable new drug target (Terrön, J. A. Idrugs, 1998, vol. 1, no. 3, pages 302-310: "The 5HT$_7$ receptor: A target for novel therapeutic avenues?").

5-HT$_7$ receptors have been cloned from rat, mouse, guinea pig and human cDNA and exhibit a high degree of interspecies homology (approx. 95%), but it is unique in that it has a low sequence homology with other 5-HT receptors (less than 40%). Its expression pattern, in particular structures of the central nervous system (CNS) (highest in hypothalamus (in particular suprachiasmatic nuclei) and thalamus) and other peripheral tissues (spleen, kidney, intestinal, heart and coronary artheryy), implicates the 5-HT$_7$ receptor in a variety of functions and pathologies. This idea is reinforced by the fact that several therapeutic agents, such as tricyclic antidepressants, typical and atypical antipsychotics and some 5-HT$_2$ receptor antagonists, display moderate to high affinity for both recombinant and functional 5-HT$_7$ receptors.

Functionally, the 5-HT$_7$ receptor has been implicated in regulation of circadian rhythms in mammals (Lovenberg, T. W. et al. Neuron, 1993, 11:449-458 "A novel adenylyl cyclase-activating serotonin receptor (5-HT$_7$) implicated in the regulation of circadian rhythms"). It is known that disruption of circadian rhythms is related to a number of CNS disorders including depression, seasonal affective disorder, sleep disorders, shift worker syndrome and jet lag among others.

Distribution and early pharmacological data also suggest that the 5-HT$_7$ receptor is involved in the vasodilatation of blood vessels. This has been demonstrated in vivo (Terrön, J. A., Br J Pharmacol, 1997, 121:563-571 "Role of 5-HT$_7$ receptors in the long lasting hypotensive response induced by 5-hydroxytryptamine in the rat"). Thus selective 5-HT$_7$ receptor agonists have a potential as novel hypertensive agents.

The 5-HT$_7$ receptor has also been related with the pathophysiology of migraine through smooth muscle relaxation of cerebral vessels (Schoeffter, P. et al., 1996, Br J Pharmacol, 117:993-994; Terrön, J. A., 2002, Eur. J. Pharmacol., 439:1-11 "Is the 5-HT$_7$ receptor involved in the pathogenesis and prophylactic treatment of migraine?"). In a similar manner, involvement of 5-HT$_7$ in intestinal and colon tissue smooth muscle relaxation makes this receptor a target for the treatment of irritable bowel syndrome (De Ponti, F. et al., 2001, Drugs, 61:317-332 "Irritable bowel syndrome. New agents targeting serotonin receptor subtypes"). Recently, it has also been related to urinary incontinence (British J. of Pharmacology, September 2003, 140(1) 53-60: "Evidence for the involvement of central 5HT-7 receptors in the micurition reflex in anaesthetized female rats").

In view of the potential therapeutic applications of agonists or antagonists of the 5HT$_7$ receptor, a great effort has been directed to find selective ligands. Despite intense research efforts in this area, very few compounds with selective 5-HT$_7$ antagonist activity have been reported (Wesolowska, A., Polish J. Pharmacol., 2002, 54: 327-341, "In the search for selective ligands of 5-HT$_5$, 5-HT$_6$ and 5-HT$_7$ serotonin receptors"), yet even fewer 5-HT7-Agonists.

There is still a need to find compounds that have pharmacological activity towards the receptor 5-HT$_7$, being both effective and selective, and having good "drugability" properties, i.e. good pharmaceutical properties related to administration, distribution, metabolism and excretion.

Thus, it was an object of the present invention to provide novel compounds that are suitable in particular as active substances in medicaments.

Said object was achieved by providing an indane-amine derivative of general formula (I)

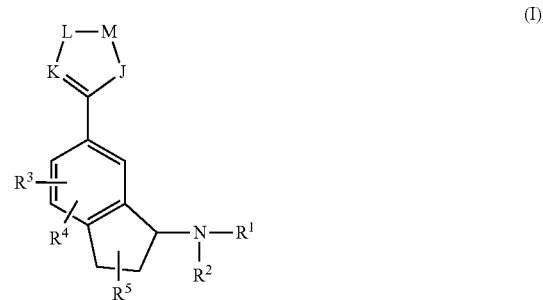

wherein
K-L-M-J together form
=CH—X—Y=CH—; in which any suitable H may be substituted by R$^6$ and/or R$^7$, and in which X is selected from NR$^8$, O or S, while Y is selected from N or CH;
=CH—X—Y—C(O)—; in which any suitable H may be substituted by R$^6$ and in which one of X and Y is NR$^8$, while the other is selected from NR$^{8a}$, S or O;
=CH—X—Y—C(O)—; in which one of X and Y is CH$_2$, while the other is selected from NR$^8$, S or O, in which any suitable H may be substituted by R$^6$ and/or R$^7$;
=CR$^6$—N=N—C(O)—;
=CR$^9$—CH=CH—CH=CH—; in which any suitable H may be substituted by R$^6$;
=CR$^9$—CH=CH—CH=CR$^{9a}$—; in which any suitable H may be substituted by R$^6$;
=CH—X=Y—CH=CH—; in which any suitable H may be substituted by R$^6$ and/or R$^7$, and in which one of X or Y is selected from N, while the other is selected from N or CH;
=CH—X=Y—CH$_2$—CH$_2$—; in which any suitable H may be substituted by R$^6$ and/or R$^7$, and in which one of X or Y is selected from N, while the other is selected from N or CH;
=CH—X—Y—CH=CH—; in which any suitable H may be substituted by R$^6$ and/or R$^7$, and in which one of X or Y is selected from NR$^8$, O or S while the other is selected from NR$^{8a}$ or CH$_2$;

=CH—X—Y—CH$_2$—CH$_2$—; in which any suitable H may be substituted by R$^6$ and/or R$^7$, and in which one of X or Y is selected from NR$^8$, O or S while the other is selected from NR$^{8a}$ or CH$_2$;

=CH—X—CH$_2$—Y=CH—; in which any suitable H may be substituted by R$^6$ and/or R$^7$, and in which X is selected from NR$^8$, O or S while Y is selected from N or CH;

=CH—X—CH=Y—CH$_2$—; in which any suitable H may be substituted by R$^6$ and/or R$^7$, and in which X is selected from NR$^8$, O or S while Y is selected from N or CH;

=CH—N=CH—Y=CH—; in which any suitable H may be substituted by R$^6$ and/or R$^7$;

=CH—X—CH$_2$—Y—CH$_2$—; in which any suitable H may be substituted by R$^6$ and/or R$^7$, and in which one of X or Y is selected from NR$^8$, O or S while the other is selected from NR$^{8a}$, O, S or CH$_2$;

R$^1$ and R$^2$ each are independently selected from the group consisting of hydrogen; or a linear or branched, saturated or unsaturated, optionally at least mono-substituted aliphatic radical;

or

R$^1$ and R$^2$ together with the bridging nitrogen atom form an saturated or unsaturated, optionally at least mono-substituted 5- or 6-membered-heterocyclic ring, which may be condensed with an optionally at least mono-substituted mono- or polycyclic ringsystem;

R$^3$, R$^4$ and R$^5$ are independently from each other selected from hydrogen; halogen, OH, SH, NH$_2$; a linear or branched, saturated or unsaturated, optionally at least mono-substituted aliphatic radical; or O—R with R being a linear or branched, saturated or unsaturated, optionally at least mono-substituted aliphatic radical;

R$^6$ and R$^7$ are independently from each other selected from hydrogen; halogen, OH, SH, NH$_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH;

R$^8$ and R$^{8a}$ are independently from each other selected from hydrogen; an aliphatic radical, which is linear or branched, saturated or unsaturated, and optionally at least mono-substituted by F, Cl, Br, I, SH or OH; or —R'—O—R" with R' and R" independently from one another being a C$_{1-6}$-alkyl radical, which is linear or branched, and optionally at least mono-substituted by F, Cl, Br, I, SH or OH;

R$^9$ and R$^{9a}$ are independently from each other selected from halogen; an aliphatic radical, which is linear or branched, saturated or unsaturated, and optionally at least mono-substituted by F, Cl, Br, I, SH or OH;; or O—R with R being an aliphatic radical, which is linear or branched, saturated or unsaturated, and optionally at least mono-substituted by F, Cl, Br, I, SH or OH;

optionally in form of one of its stereoisomers, preferably enantiomers or diastereomers, its racemate or in form of a mixture of at least two of its stereoisomers, preferably enantiomers or diastereomers, in any mixing ratio, or a salt, preferably a physiologically acceptable salt thereof, or a corresponding solvate, respectively; or a halide salt thereof, in which NR$^1$R$^2$ of general formula (I) is substituted by an additional methyl to form with R$^1$ and R$^2$ being CH$_3$ a trimethyl-ammonium-radical.

These compounds show a high affinity to the 5HT$_7$ Receptor as well as a high selectivity for this receptor in comparison to e.g. the 5HT$_6$, the Sigma 1, the α2, and the 5HT$_1$ Receptor, thus having a higher affinity to the 5HT$_7$ receptor. In addition some of these compounds show an agonistic activity on this receptor.

A "mono- or polycyclic ring-system" according to the present invention means a mono- or polycyclic hydrocarbon ring-system that may be saturated, unsaturated or aromatic. If the ring system is polycyclic, each of its different rings may show a different degree of saturation, i.e. it may be saturated, unsaturated or aromatic. Optionally each of the rings of the mono- or polycyclic ring system may contain one or more heteroatoms as ring members, which may be identical or different and which can preferably be selected from the group consisting of N, O, S and P, more preferably be selected from the group consisting of N, O and S. Preferably the polycyclic ring-system may comprise two rings that are condensed. The rings of the mono- or polycyclic ring-sytem are preferably 5- or 6-membered.

An "aryl", "aryl radical" or group is understood as meaning ring systems with at least one aromatic ring but without heteroatoms even in only one of the rings. Examples are phenyl, naphthyl, fluoranthenyl, fluorenyl, tetralinyl or indanyl, in particular 9H-fluorenyl or anthracenyl radicals, which can be unsubstituted or monosubstituted or polysubstituted.

In the context of this invention "cycloalkyl radical" or group is understood as meaning saturated and unsaturated (but not aromatic) cyclic hydrocarbons (without a heteroatom in the ring), which can be unsubstituted or mono- or polysubstituted. Furthermore, C$_{3-4}$-cycloalkyl represents C$_3$- or C$_4$-cycloalkyl, C$_{3-5}$-cycloalkyl represents C$_3$-, C$_4$- or C$_5$-cycloalkyl, C$_{3-6}$-cycloalkyl represents C$_3$-, C$_4$-, C$_5$- or C$_6$-cycloalkyl, C$_{3-7}$-cycloalkyl represents C$_3$-, C$_4$-, C$_5$-, C$_6$- or C$_7$-cycloalkyl, C$_{3-8}$-cycloalkyl represents C$_3$-, C$_4$-, C$_5$-, C$_6$-, C$_7$- or C$_8$-cycloalkyl, C$_{4-5}$-cycloalkyl represents C$_4$- or C$_5$-cycloalkyl, C$_{4-6}$-cycloalkyl represents C$_4$-, C$_5$- or C$_6$-cycloalkyl, C$_{4-7}$-cycloalkyl represents C$_4$-, C$_5$-, C$_6$- or C$_7$-cycloalkyl, C$_{4-8}$-cycloalkyl represents C$_4$-, C$_5$-, C$_6$-, C$_7$- or C$_8$-cycloalkyl C$_{5-6}$-cycloalkyl represents C$_5$- or C$_6$-cycloalkyl and C$_{5-7}$-cycloalkyl represents C$_5$-, C$_6$- or C$_7$-cycloalkyl. However, mono- or polyunsaturated, preferably monounsaturated, cycloalkyls also in particular fall under the term cycloalkyl as long as the cycloalkyl is not an aromatic system. The cycloalkyl radicals are preferably cyclopropyl, 2-methylcyclopropyl, cyclopropylmethyl, cyclobutyl, cyclopentyl, cyclopentylmethyl, cyclohexyl, cycloheptyl, cyclooctyl, and also adamantly.

A "heterocyclyl", a "heterocyclyl radical" or group or "heterocyclic ring system" is understood as meaning heterocyclic ring systems which contain one or more heteroatoms from the group consisting of nitrogen, oxygen and/or sulfur in the ring or ringsystem, and can also be mono- or polysubstituted. The ringsystem may consist either of only one saturated or unsaturated or even aromatic ring or may consist of 2, 3 or 4 saturated or unsaturated or even aromatic rings, which are condensed in that between two or more of the rings ring members are shared. Examples which may be mentioned from the group of heterocyclyls are furan, benzofuran, thiophene, benzothiophene, pyrrole, pyridine, pyrimidine, pyrazine, quinoline, isoquinoline, phthalazine, benzo-1,2,5-thiadiazole, imidazo-thiazole, benzothiazole, indole, benzotriazole, benzodioxolane, benzodioxane, carbazole and quinazoline.

In connection with mono- or polycyclic ring-system, aryl radical, cycloalkyl radical, or heterocyclyl radical, "substituted" is understood—unless defined otherwise—as meaning replacement of at least one hydrogen radical on the ring-system of the mono- or polycyclic ring-system, the aryl radical, the cycloalkyl radical, or the heterocyclyl radical by OH, SH, =O, halogen (F, Cl, Br, I), CN, $NO_2$, COOH; $NR_xR_y$, with $R_x$ and $R_y$ independently being either H or a saturated or unsaturated, linear or branched, substituted or unsubstituted $C_{1-6}$-alkyl; by a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl; a saturated or unsaturated, linear or branched, substituted or unsubstituted —C(O)—O—$C_{1-6}$-alkyl; a substituted or unsubstituted phenyl. Within that "monosubstituted" means the substitution of exactly one hydrogen radical, whereas "polysubstituted" means the substitution of more than one hydrogen radical with "polysubstituted" radicals being understood as meaning that the replacement takes effect both on different and on the same atoms several times with the same or different substituents. Therefore, "optionally at least monsubstituted" means either "not substituted" if the option is not fulfilled, "monosubstituted" or "polysubstituted".

In connection with aryl radical, cycloalkyl radical, or heterocyclyl radical, "condensed with" is understood as meaning that the ring-system of the aryl radical, the cycloalkyl radical, or the heterocyclyl radical is sharing two atoms (one) of its ring(s) with a ring of the mono- or polycyclic ring-system it is condensed with.

Aliphatic radicals/groups, as referred to in the present invention, are optionally mono- or polysubstituted and may be branched or linear, saturated or unsaturated. Aliphatic radicals, as defined in the present invention, include alkyl, alkenyl and alkinyl radicals. Unsaturated aliphatic radicals, as defined in the present invention, include alkenyl and alkinyl radicals. Preferred aliphatic radicals according to the present invention include but are not restricted to methyl, ethyl, vinyl (ethenyl), ethinyl, propyl, n-propyl, isopropyl, allyl (2-propenyl), 1-propinyl, methylethyl, butyl, n-butyl, iso-butyl, sec-butyl, tert-butyl butenyl, butinyl, 1-methylpropyl, 2-methylpropyl, 1,1-dimethylethyl, pentyl, n-pentyl, 1,1-dimethylpropyl, 1,2-dimethylpropyl, 2,2-dimethylpropyl, hexyl, 1-methylpentyl, n-heptyl, n-octyl, n-nonyl and n-decyl.

In the context of this invention, "alkyl", "alkyl radical" or group is understood as meaning saturated, linear or branched hydrocarbons, which can be unsubstituted or mono- or polysubstituted. Thus unsaturated alkyl is understood to encompass alkenyl and alkinyl groups, like e.g. —CH=CH—$CH_3$ or —C≡C—$CH_3$, while saturated alkyl encompasses e.g. —$CH_3$ and —$CH_2$—$OH_3$. In these radicals, $C_{1-2}$-alkyl represents $C_1$- or $C_2$-alkyl, $C_{1-3}$-alkyl represents $C_1$-, $C_2$- or $C_3$-alkyl, $C_{1-4}$-alkyl represents $C_1$-, $C_2$-, $C_3$- or $C_4$-alkyl, $C_{1-5}$-alkyl represents $C_1$-, $C_2$-, $C_3$-, $C_4$-, or $C_5$-alkyl, $C_{1-6}$-alkyl represents $C_1$-, $C_2$-, $C_3$-, $C_4$-, $C_5$- or $C_6$-alkyl, $C_{1-7}$-alkyl represents $C_1$-, $C_2$-, $C_3$-, $C_4$-, $C_5$-, $C_6$- or $C_7$-alkyl, $C_{1-8}$-alkyl represents $C_1$-, $C_2$-, $C_3$-, $C_4$-, $C_5$-, $C_6$-, $C_7$- or $C_8$-alkyl, $C_{1-10}$-alkyl represents $C_1$-, $C_2$-, $C_3$-, $C_4$-, $C_5$-, $C_6$-, $C_7$-, $C_8$-, $C_9$- or $C_{10}$-alkyl and $C_{1-18}$-alkyl represents $C_1$, $C_2$-, $C_3$-, $C_4$-, $C_5$-, $C_6$-, $C_7$-, $C_8$-, $C_9$-, $C_{10}$-, $C_{11}$-, $C_{12}$-, $C_{13}$-, $C_{14}$-, $C_{15}$-, $C_{16}$-, $C_{17}$- or $C_{18}$-alkyl. The alkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc.

In connection with alkylene, alkyl or aliphatic radical or group—unless defined otherwise—the term "substituted" in the context of this invention is understood as meaning replacement of at least one hydrogen radical by F, Cl, Br, I, $NH_2$, SH or OH; within that "monosubstituted" means the substitution of exactly one hydrogen radical, whereas "polysubstituted" means the substitution of more than one hydrogen radical with "polysubstituted" radicals being understood as meaning that the replacement takes effect both on different and on the same atoms several times with the same or different substituents, for example three times on the same C atom, as in the case of $CF_3$, or at different places, as in the case of e.g. —CH(OH)—CH=CH—$CHCl_2$. Therefore, "optionally at least monsubstituted" means either "not substituted" if the option is not fulfilled, "monosubstituted" or "polysubstituted".

The term "alkylene" is understood as meaning a divalent alkyl group like —$CH_2$— or —$CH_2$—$OH_2$—, with $(CH_2)_{3-6}$ being understood as meaning —$CH_2$—$OH_2$—$OH_2$—, —$CH_2$—$CH_2$—$CH_2$—$CH_2$—, —$CH_2$—$CH_2$—$CH_2$—$OH_2$—$OH_2$— and —$CH_2$—$OH_2$—$OH_2$—$OH_2$—$OH_2$—, $(CH_2)_{1-4}$ is to be understood as meaning —$CH_2$—, —$CH_2$—$OH_2$—, —$CH_2$—$OH_2$—$OH_2$— and —$CH_2$—$OH_2$—$OH_2$—$OH_2$—, $(CH_2)_{4-5}$ is to be understood as meaning —$CH_2$—$OH_2$—$OH_2$—$OH_2$— and —$CH_2$—$OH_2$—$OH_2$—$OH_2$—$OH_2$—, etc. An "alkylene" may also be unsaturated.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes which are complexed via ionic interactions.

The term "physiologically acceptable salt" means in the context of this invention any salt that is physiologically tolerated (most of the time meaning not being toxic-especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with NH4, but in particular (mono)- or (di)sodium, (mono)- or (di)potassium, magnesium or calcium salts.

These physiologically acceptable salts can also be formed with anions or acids in the context of this invention is understood as meaning salts of at least one of the compounds used according to the invention—usually protonated, for example on the nitrogen—as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be in crystalline form or either as free compounds or as solvates and it is intended that those forms are within the scope of the present invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent) especially including hydrates and alcoholates, e.g. methanolate.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon or $^{15}N$-enriched nitrogen are within the scope of this invention.

Any compound that is a prodrug of a compound of formula (I) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given compound are known to those skilled in the art and can be found e.g. in Krogsgaard-Larsen et al. "Textbook of Drug design and Discovery" Taylor & Francis (April 2002).

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I) or, or of its salts, solvates or prodrugs.

Particularly preferred are compounds according to the invention which are compounds of general formula (Ia),

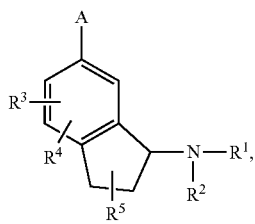

(Ia)

wherein
A is a compound selected from the following group

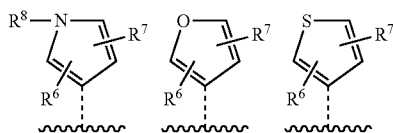

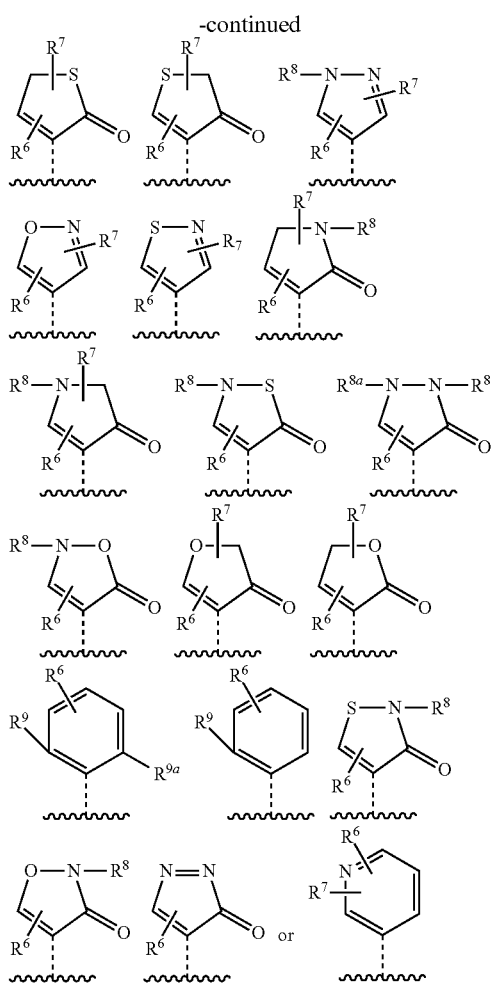

-continued $R^1$ and $R^2$ each are independently selected from the group consisting of hydrogen; or a linear or branched, saturated or unsaturated, optionally at least mono-substituted aliphatic radical; or $R^1$ and $R^2$ together with the bridging nitrogen atom form an saturated or unsaturated, optionally at least mono-substituted 5- or 6-membered-heterocyclic ring, which may be condensed with an optionally at least mono-substituted mono- or polycyclic ringsystem, $R^3$, $R^4$ and $R^5$ are independently from each other selected from hydrogen; halogen, OH, SH, $NH_2$; a linear or branched, saturated or unsaturated, optionally at least mono-substituted aliphatic radical; or O—R with R being a linear or branched, saturated or unsaturated, optionally at least mono-substituted aliphatic radical;

$R^6$ and $R^7$ are independently from each other selected from hydrogen; halogen, OH, SH, $NH_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH;

$R^8$ and $R^{8a}$ are independently from each other selected from hydrogen; an aliphatic radical, which is linear or branched, saturated or unsaturated, and optionally at least mono-substituted by F, Cl, Br, I, SH or OH; or —R'—O—R" with R' and R" independently from one another being a $C_{1-6}$-alkyl radical, which is linear or branched, and optionally at least mono-substituted by F, Cl, Br, I, SH or OH;

$R^9$ and $R^{9a}$ are independently from each other selected from halogen; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH.

Also the compounds of general Formula (Ia) may be optionally in form of one of its stereoisomers, preferably enantiomers or diastereomers, its racemate or in form of a mixture of at least two of its stereoisomers, preferably enantiomers or diastereomers, in any mixing ratio, or a salt, preferably a physiologically acceptable salt thereof, or a corresponding solvate, respectively; or a halide salt thereof, in which $NR^1R^2$ of general formula (I) is substituted by an additional methyl to form with $R^1$ and $R^2$ being $CH_3$ a trimethyl-ammonium-radical.

Also particularly preferred is a compound according to the invention, which is a compound according to Formula Ia, wherein A is a compound selected from the following group

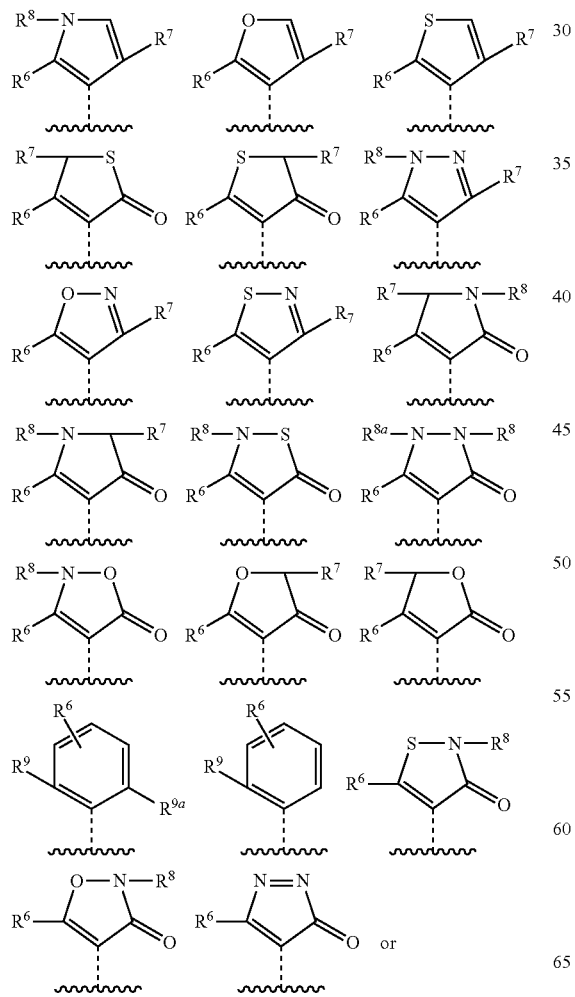

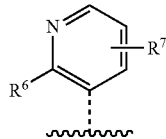

$R^1$ and $R^2$ each are independently selected from the group consisting of hydrogen; or a linear or branched, saturated or unsaturated, optionally at least mono-substituted aliphatic radical; or $R^1$ and $R^2$ together with the bridging nitrogen atom form an saturated or unsaturated, optionally at least mono-substituted 5- or 6-membered-heterocyclic ring, which may be condensed with an optionally at least mono-substituted mono- or polycyclic ringsystem, $R^3$, $R^4$ and $R^5$ are independently from each other selected from hydrogen; halogen, OH, SH, $NH_2$; a linear or branched, saturated or unsaturated, optionally at least mono-substituted aliphatic radical; or O—R with R being a linear or branched, saturated or unsaturated, optionally at least mono-substituted aliphatic radical;

$R^6$ and $R^7$ are independently from each other selected from hydrogen; halogen, OH, SH, $NH_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH;

$R^8$ and $R^{8a}$ are independently from each other selected from hydrogen; an aliphatic radical, which is linear or branched, saturated or unsaturated, and optionally at least mono-substituted by F, Cl, Br, I, SH or OH; or —R'—O—R" with R' and R" independently from one another being a $C_{1-6}$-alkyl radical, which is linear or branched, and optionally at least mono-substituted by F, Cl, Br, I, SH or OH;

$R^9$ and $R^{9a}$ are independently from each other selected from halogen; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH.

Also particularly preferred is a compound according to the invention, which is a compound according to Formula Ia, wherein A is a compound selected from the following group

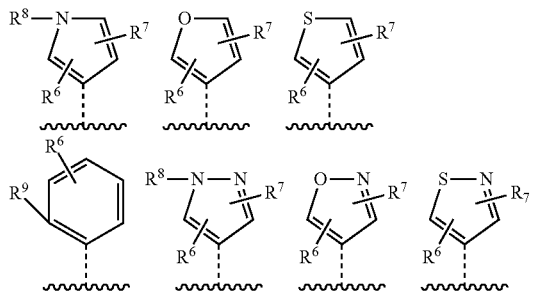

-continued

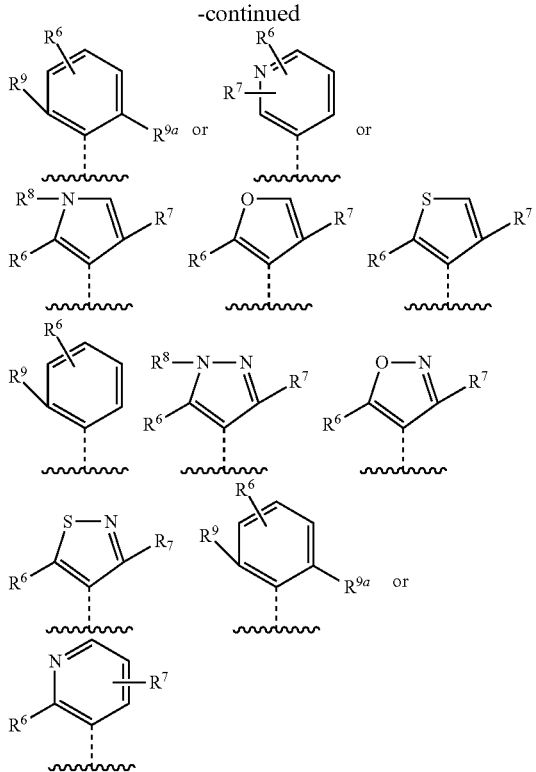

R¹ and R² each are independently selected from the group consisting of hydrogen; or a linear or branched, saturated or unsaturated, optionally at least mono-substituted aliphatic radical; or R¹ and R² together with the bridging nitrogen atom form an saturated or unsaturated, optionally at least mono-substituted 5- or 6-membered-heterocyclic ring, which may be condensed with an optionally at least mono-substituted mono- or polycyclic ringsystem, R³, R⁴ and R⁵ are independently from each other selected from hydrogen; halogen, OH, SH, NH₂; a linear or branched, saturated or unsaturated, optionally at least mono-substituted aliphatic radical; or O—R with R being a linear or branched, saturated or unsaturated, optionally at least mono-substituted aliphatic radical;

R⁶ and R⁷ are independently from each other selected from hydrogen; halogen, OH, SH, NH₂; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH;

R⁸ and R⁸ᵃ are independently from each other selected from hydrogen; an aliphatic radical, which is linear or branched, saturated or unsaturated, and optionally at least mono-substituted by F, Cl, Br, I, SH or OH; or —R'—O—R" with R' and R" independently from one another being a C₁₋₆-alkyl radical, which is linear or branched, and optionally at least mono-substituted by F, Cl, Br, I, SH or OH R⁹ and R⁹ᵃ are independently from each other selected from halogen; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH.

Also particularly preferred is a compound according to the invention, which is a compound of GROUP A according to Formula Ia, wherein A is a compound selected from the following group

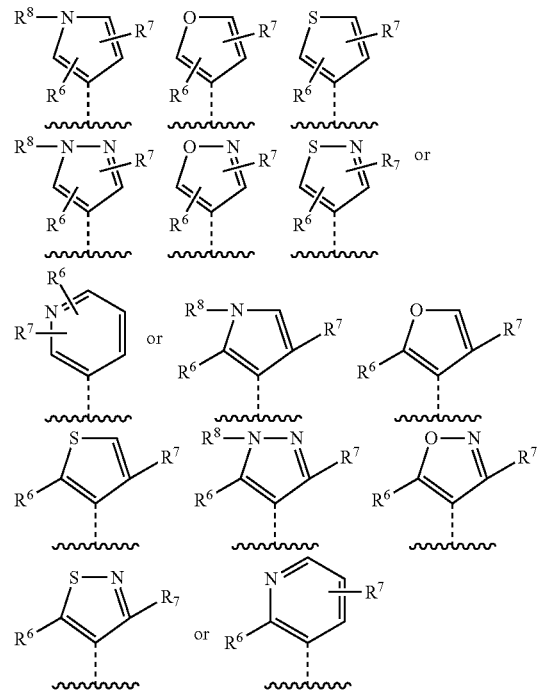

R¹ and R² each are independently selected from the group consisting of hydrogen; or a linear or branched, saturated or unsaturated, optionally at least mono-substituted aliphatic radical; or R¹ and R² together with the bridging nitrogen atom form an saturated or unsaturated, optionally at least mono-substituted 5- or 6-membered-heterocyclic ring, which may be condensed with an optionally at least mono-substituted mono- or polycyclic ringsystem;

R³, R⁴ and R⁵ are independently from each other selected from hydrogen; halogen, OH, SH, NH₂; a linear or branched, saturated or unsaturated, optionally at least mono-substituted aliphatic radical; or O—R with R being a linear or branched, saturated or unsaturated, optionally at least mono-substituted aliphatic radical;

R⁶ and R⁷ are independently from each other selected from hydrogen; halogen, OH, SH, NH₂; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH;

R⁸ is selected from hydrogen; or an aliphatic radical, which is linear or branched, saturated or unsaturated, and optionally at least mono-substituted by F, Cl, Br, I, SH or OH; or —R'—O—R" with R' and R" independently from one another being a C₁₋₆-alkyl radical, which is linear or branched, and optionally at least mono-substituted by F, Cl, Br, I, SH or OH.

Also particularly preferred is a compound according to the invention, which is a compound of GROUP B according to Formula Ia, wherein A is a compound selected from the following group

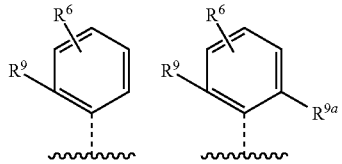

$R^1$ and $R^2$ each are independently selected from the group consisting of hydrogen; or a linear or branched, saturated or unsaturated, optionally at least mono-substituted aliphatic radical; or $R^1$ and $R^2$ together with the bridging nitrogen atom form an saturated or unsaturated, optionally at least mono-substituted 5- or 6-membered-heterocyclic ring, which may be condensed with an optionally at least mono-substituted mono- or polycyclic ringsystem, $R^3$, $R^4$ and $R^5$ are independently from each other selected from hydrogen; halogen, OH, SH, $NH_2$; a linear or branched, saturated or unsaturated, optionally at least mono-substituted aliphatic radical; or O—R with R being a linear or branched, saturated or unsaturated, optionally at least mono-substituted aliphatic radical;

$R^6$ is selected from hydrogen; halogen, OH, SH, $NH_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH;

$R^9$ and $R^{9a}$ are independently from each other selected from halogen; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH.

Also particularly preferred is a compound according to the invention, which is a compound of GROUP A or GROUP B according to Formula Ia, wherein $R^1$ and $R^2$ each are independently selected from the group consisting of hydrogen; or a linear or branched, optionally at least mono-substituted $C_{1-4}$-alkyl radical; or $R^1$ and $R^2$ together with the bridging nitrogen atom form an saturated or unsaturated, optionally at least mono-substituted 5- or 6-membered-heterocyclic ring;

preferably in that $R^1$ and $R^2$ are each independently selected from the group consisting of hydrogen; or a linear or branched $C_{1-4}$-alkyl radical; or $R^1$ and $R^2$ together with the bridging nitrogen atom form an saturated or unsaturated, optionally at least mono-substituted 5- or 6-membered-heterocyclic ring;

more preferably in that $R^1$ and $R^2$ are each independently selected from the group consisting of hydrogen, $CH_3$, $O_2H_5$ or $O_3H_7$.

Also particularly preferred is a compound according to the invention, which is a compound of GROUP A or GROUP B according to Formula Ia, wherein $R^3$, $R^4$ and $R^5$ are independently from each other selected from hydrogen; halogen, OH, SH, $NH_2$; a linear or branched, optionally at least mono-substituted $C_{1-4}$-alkyl radical; or O—R with R being a linear or branched, optionally at least mono-substituted $O_{14}$-alkyl radical;

preferably in that $R^3$, $R^4$ and $R^5$ are independently from each other selected from H, F, Cl, Br, I, OH, SH, $NH_2$, $CH_3$, $C_2H_5$, $C_3H_7$, $C_4H_9$, $OCH_3$, $OC_2H_5$, $OC_3H_7$ or $OC_4H_9$, more preferably in that $R^3$, $R^4$ and $R^5$ are H.

Also particularly preferred is a compound according to the invention, which is a compound of GROUP A according to Formula Ia, wherein $R^6$ and $R^7$ are independently from each other selected from hydrogen; halogen, OH, SH, $NH_2$; a $C_{1-4}$-alkyl radical, which is linear or branched, and optionally at least mono-substituted by F, Cl, Br, I, SH or OH; or O—R with R being a $C_{1-4}$-alkyl radical, which is linear or branched, and optionally at least mono-substituted by F, Cl, Br, I, SH or OH;

preferably in that $R^6$ and $R^7$ are independently from each other selected from H, F, Cl, Br, I, OH, SH, $NH_2$, $CH_3$, $C_2H_5$, $C_3H_7$, $C_4H_9$, $OCH_3$, $OC_2H_5$, $OC_3H_7$ or $OC_4H_9$;

more preferably in that $R^6$ and $R^7$ are independently from each other selected from H, or $CH_3$.

Also particularly preferred is a compound according to the invention, which is a compound of GROUP A according to Formula Ia, wherein $R^8$ is selected from hydrogen; a $C_{1-4}$-alkyl radical, which is linear or branched, and optionally at least mono-substituted by F, Cl, Br, I, SH or OH; or —$(CH_2)_p$—O—$(CH_2)_q$ with p and q independently from one another being 1, 2, 3 or 4;

preferably in that $R^8$ is selected from H, F, Cl, Br, I, OH, SH, $NH_2$, $CH_3$, $O_2H_5$, $C_3H_7$, $C_4H_9$, $CH_2$—O—$CH_3$ or $CH_2$—O—$C_2H_5$;

more preferably in that $R^8$ is selected from H, $CH_3$, $C_2H_5$, $C_3H_7$, $C_4H_9$, or $CH_2$—O—$CH_3$.

Also particularly preferred is a compound according to the invention, which is a compound of GROUP A according to Formula Ia, selected from Dimethyl-[6-(1,3,5-trimethyl-1H-pyrazol-4-yl)-indan-1-yl]-amine;

(R) Dimethyl-[6-(1,3,5-trimethyl-1H-pyrazol-4-yl)-indan-1-yl]-amine;

(S) Dimethyl-[6-(1,3,5-trimethyl-1H-pyrazol-4-yl)-indan-1-yl]-amine;

Methyl-[6-(1,3,5-trimethyl-1H-pyrazol-4-yl)-indan-1-yl]-amine;

6-(1,3,5-Trimethyl-1H-pyrazol-4-yl)-indan-1-ylamine;

Diethyl-[6-(1,3,5-trimethyl-1H-pyrazol-4-yl)-indan-1-yl]-amine;

Dipropyl-[6-(1,3,5-trimethyl-1H-pyrazol-4-yl)-indan-1-yl]-amine;

[6-(3,5-Dimethyl-1H-pyrazol-4-yl)-indan-1-yl]-dimethyl-amine;

[6-(3,5-Dimethyl-1H-pyrazol-4-yl)-indan-1-yl]-methyl-amine;

[6-(3,5-Dimethyl-isoxazol-4-yl)-indan-1-yl]-dimethyl-amine;

[6-(3,5-Dimethyl-isoxazol-4-yl)-indan-1-yl]-methyl-amine;

[6-(1-Ethyl-3,5-dimethyl-1H-pyrazol-4-yl)-indan-1-yl]-dimethyl-amine;

[6-(1-Ethyl-3,5-dimethyl-1H-pyrazol-4-yl)-indan-1-yl]-methyl-amine;
[6-(3,5-Dimethyl-1-propyl-1H-pyrazol-4-yl)-indan-1-yl]-dimethyl-amine;
[6-(3,5-Dimethyl-1-propyl-1H-pyrazol-4-yl)-indan-1-yl]-methyl-amine;
[6-(1-Isopropyl-3,5-dimethyl-1H-pyrazol-4-yl)-indan-1-yl]-dimethyl-amine;
[6-(1-Isopropyl-3,5-dimethyl-1H-pyrazol-4-yl)-indan-1-yl]-methyl-amine;
[6-(1-Isobutyl-3,5-dimethyl-1H-pyrazol-4-yl)-indan-1-yl]-dimethyl-amine:
[6-(1-Isobutyl-3,5-dimethyl-1H-pyrazol-4-yl)-indan-1-yl]-methyl-amine;
[6-(1-Methoxymethyl-3,5-dimethyl-1H-pyrazol-4-yl)-indan-1-yl]-dimethyl-amine; or
[6-(1-Methoxymethyl-3,5-dimethyl-1H-pyrazol-4-yl)-indan-1-yl]-methyl-amine; or
Trimethyl-[6-(1,3,5-trimethyl-1H-pyrazol-4-yl)-indan-1-yl]-ammonium iodide;
(S) Methyl-[6-(1,3,5-trimethyl-1H-pyrazol-4-yl)-indan-1-yl]-amine;
(R) Methyl-[6-(1,3,5-trimethyl-1H-pyrazol-4-yl)-indan-1-yl]-amine;
[6-(2-Methoxy-pyridin-3-yl)-indan-1-yl]-dimethyl-amine;
[6-(2-Methoxy-pyridin-3-yl)-indan-1-yl]-methyl-amine;
Dimethyl-(6-piperidin-1-yl-indan-1-yl)-amine; hydrochloride; or
Dimethyl-(6-pyrrolidin-1-yl-indan-1-yl)-amine;
optionally in form of a salt, preferably a physiologically acceptable salt, more preferably in form of a physiologically acceptable acid addition salt, most preferably a hydrochloride salt, or a corresponding solvate; or a halide salt thereof, in which $NR^1R^2$ of general formula (I) is substituted by an additional methyl to form with $R^1$ and $R^2$ being $CH_3$ a trimethyl-ammonium-radical.

Also particularly preferred is a compound according to the invention, which is a compound of GROUP B according to Formula Ia, wherein
$R^6$ is selected from hydrogen; halogen, OH, SH, $NH_2$; a $C_{1-4}$-alkyl radical, which is linear or branched, and optionally at least mono-substituted by F, Cl, Br, I, SH or OH; or O—R with R being a $C_{1-4}$-alkyl radical, which is linear or branched, and optionally at least mono-substituted by F, Cl, Br, I, SH or OH;
preferably in that
$R^6$ is selected from H, F, Cl, Br, I, OH, SH, $NH_2$, $CH_3$, $C_2H_5$, $C_3H_7$, $C_4H_9$, $OCH_3$, $OC_2H_5$, $OC_3H_7$ or $OC_4H_9$;
more preferably in that
$R^6$ is H.

Also particularly preferred is a compound according to the invention, which is a compound of GROUP B according to Formula Ia, wherein
$R^9$ and $R^{9a}$ are independently from each other selected from halogen; a $C_{1-4}$-alkyl radical, which is linear or branched, and optionally at least mono-substituted by F, Cl, Br, I, SH or OH; or O—R with R being a $C_{1-4}$-alkyl radical, which is linear or branched, and optionally at least mono-substituted by F, Cl, Br, I, SH or OH;
preferably in that
$R^9$ and $R^{9a}$ are independently from each other selected from F, Cl, Br, I, $CH_3$, $C_2H_5$, $C_3H_7$, $C_4H_9$, $OCH_3$, $OC_2H_5$, $OC_3H_7$ or $OC_4H_9$;
more preferably in that
$R^9$ and $R^{9a}$ are independently from each other selected from F, Cl, $CH_3$, $CF_3$ or $OCH_3$.

Also particularly preferred is a compound according to the invention, which is a compound of GROUP B according to Formula Ia selected from
[6-(2,6-Dimethoxy-phenyl)-indan-1-yl]-dimethyl-amine;
[6-(2,6-Dimethoxy-phenyl)-indan-1-yl]-methyl-amine;
[6-(2-Methoxy-phenyl)-indan-1-yl]-dimethyl-amine;
[6-(2-Methoxy-phenyl)-indan-1-yl]-methyl-amine;
[6-(2,6-Dimethyl-phenyl)-indan-1-yl]-dimethyl-amine;
[6-(2,6-Dimethyl-phenyl)-indan-1-yl]-methyl-amine;
[6-(2,6-Dichloro-phenyl)-indan-1-yl]-dimethyl-amine;
[6-(2,6-Dichloro-phenyl)-indan-1-yl]-methyl-amine;
[6-(2,6-Difluoro-phenyl)-indan-1-yl]-dimethyl-amine;
[6-(2,6-Difluoro-phenyl)-indan-1-yl]-methyl-amine;
[6-(2-Chloro-6-methoxy-phenyl)-indan-1-yl]-dimethyl-amine;
[6-(2-Chloro-6-methoxy-phenyl)-indan-1-yl]-methyl-amine;
[6-(2,6-Bis-trifluoromethyl-phenyl)-indan-1-yl]-dimethyl-amine; or
[6-(2,6-Bis-trifluoromethyl-phenyl)-indan-1-yl]-methyl-amine;
optionally in form of a salt, preferably a physiologically acceptable salt, more preferably in form of a physiologically acceptable acid addition salt, most preferably a hydrochloride salt, or a corresponding solvate.

optionally in form of a salt, preferably a physiologically acceptable salt, more preferably in form of a physiologically acceptable acid addition salt, most preferably a hydrochloride salt, or a corresponding solvate; or a halide salt thereof, in which $NR^1R^2$ of general formula (I) is substituted by an additional methyl to form with $R^1$ and $R^2$ being $CH_3$ a trimethyl-ammonium-radical.

In a further aspect the present invention also provides a process for the preparation of compounds of general formula (I), wherein a compound of general formula (III),

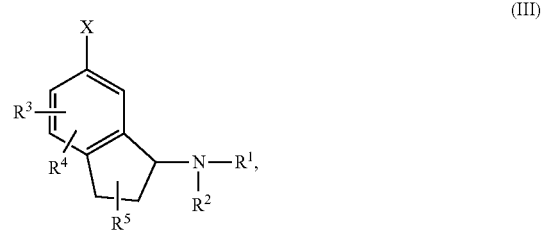

wherein $R^1$, $R^2$, $R^3$, $R^4$ and $R^5$ are as defined above, and X represents halogen, preferably bromide, OH, $OCH_3$, or an O-triflate group, is reacted with a compound of general formula IIb or IIc,

-continued

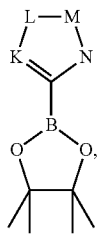
(IIc)

wherein K, L, M, and N are as defined above, to form a compound according to formula I, preferably in presence of a catalyst.

In another further aspect the present invention also provides a process for the preparation of compounds of general formula (Ia), wherein a compound of general formula (III),

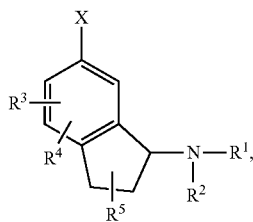
(III)

wherein $R^1$, $R^2$, $R^3$, $R^4$ and $R^5$ are as defined above, and X represents halogen, preferably bromide, OH, $OCH_3$, or an O-triflate group, is reacted with a compound of general formula II or IIa,

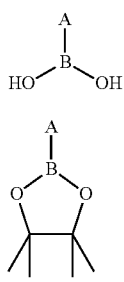
(II)

(IIa)

wherein A is as defined above, to form a compound according to formula Ia, preferably in presence of a catalyst.

In a preferred embodiment of any one of these processes
a) the catalyst is a palladium catalyst and/or
b) a ligand is present, and/or
c) the reaction is carried out in presence of at least one base, selected from organic or inorganic bases and/or
d) the reaction is carried out in a suitable reaction medium.

The compounds of general formulas (III) and (II), (IIa), (IIb) or (IIc) are either commercially available or can be produced according to methods known to those skilled in the art.

Suitable reaction media are e.g. organic solvents, such as ethers, preferably diethyl ether, dioxane, tetrahydrofurane, dimethyl glycol ether, or alcohols, e.g. methanol, ethanol, propanol, isopropanol, butanol, isobutanol, tert-butanol, or hydrocarbons, preferably benzene, toluene, xylene, hexane, cyclohexane, petroleum ether, or halogenated hydrocarbons, e.g. dichloromethane, trichloromethane, tetrachloromethane, dichloroethylene, trichloroethylene, chlorobenzene or/and other solvents preferably ethyl acetate, triethylamine, pyridine, dimethulsulfoxide, dimethylformamide, hexamethylphosphoramide, acetonitrile, acetone or nitromethane are included. Mixtures based one or more of the above mentioned solvents and water may also be used.

According to the invention, the bases that may be used in the process are generally organic or inorganic bases, preferably alkali metal hydroxides, e.g. sodium hydroxide or potassium hydroxide, or obtained from other metals such as barium hydroxide or different carbonates, preferably potassium carbonate, sodium carbonate, calcium carbonate or alkoxydes, e.g. sodium methoxide potassium methoxide, sodium ethoxide, potassium ethoxide or potassium tert-butoxide, or organic amines, preferably triethylamine, diisopropylethylamine or heterocycles, e.g. 1,4-diazabicyclo[2.2.2]octane, 1,8-diazabicyclo5.4.0]undec-7-ene, pyridine, diamino pydine, dimethylaminopyridine, methylpiperidine or morpholine. Alkali metals such as sodium or its hydrides, e.g. sodium hydride, may also be used.

In a further aspect the present invention also provides a process for the preparation of salts of compounds of general formula (I), wherein at least one compound of general formula (I) or (Ia) is reacted with an inorganic and/or organic acid, preferably in the presence of a suitable reaction medium. Suitable reaction media are the ones given above. Suitable inorganic acid are for example hydrochloric acid, hydrobromic acid, phosphoric acid, sulphuric acid, nitric acid. Suitable organic acids are e.g. citric acid, maleic acid, furmaric acid, tartaric acid or derivatives thereof, such as p-toluenesulfonic acid, methanesulfonic acid or camphersulfonic acid.

In yet a further aspect the present invention also provides a process for the preparation of salts of compounds of general formula (I), or (Ia), wherein at least one compound of general formula (I), or (Ia) having at least one acidic group is reacted with one or more suitable bases, preferably in the presence of suitable reaction medium. Suitable bases are e.g. hydroxides. Carbonates or alkoxides, which include suitable cations, derived e.g. from alkaline metals, alkaline earth metals or organic cations, e.g. $[NH_nR_{4-n}]^+$, wherein n is 0, 1, 2, 3 or 4 and R represents a branched or linear $C_{1-4}$ alkyl radical.

Solvates, preferably hydrates, of the compounds of general formula (I), or (Ia) or corresponding stereoisomers, or corresponding salts may also be obtained by standard procedures known to those skilled in the art.

If the compounds of general formula (I) or (Ia) are obtained in form of a mixture of stereoisomers, particularly enantiomers or diastereomers, said mixtures may be separated by standard procedures known to those skilled in the art, e.g. chromatographic methods of crystallization with chiral reagents.

The purification and isolation of the compounds of general formula (I) or (Ia) or a corresponding stereoisomer, or a corresponding salt, or corresponding solvate respectively, if required may be carried out by conventional methods known to those skilled in the art, e.g. chromatographic methods or recrystallization.

In another further aspect, the present invention also provides a process for the preparation of compounds of general formula (I) or especially (Ia), according to Scheme 1, wherein $R^1$, $R^2$, $R^3$, $R^4$, $R^5$ and A have the meaning given above, especially a process in which $R^3$, $R^4$ and $R^5$ are all H.

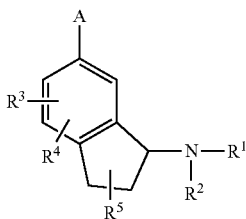

The compounds of general formula (Ia) can be prepared by catalytic cross-coupling reactions, which include the Kumada-Corriu-Tamao, Negishi, Stille, Hiyama, Suzuki-Miyaura, Heck, Sonogashira and other cross-coupling reactions known to those skilled in the art. More preferably, the compounds of general formula (Ia) can be prepared by cross-coupling Suzuki reaction of boronic acids or boronate esters of general formula (II) or (IIa),

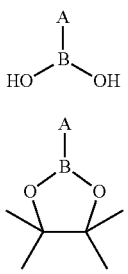

wherein A has the meaning described above, with at least one compound of general formula (III),

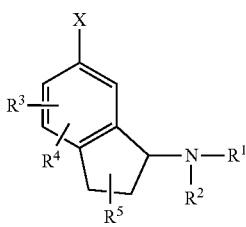

wherein $R^1$, $R^2$, $R^3$, $R^4$ and $R^5$ have the meaning given above and X represents halogen, preferably bromide, OH, OMe or O-triflate group, in a suitable reaction medium, in the presence of a palladium catalyst, a suitable ligand and at least one base. This process can be performed by subjecting the reaction mixture to reflux by conventional heating for a period of time sufficient to achieve the title compound (Ia), or by microwave radiation, preferably for 5 to 60 minutes, and at a temperature between 100 to 120° C.

Preparation of Compounds of General Formula (Iii) can be Achieved by Two Consecutive reductive amination reactions of aldehydes of general formula (IV) and (V), $R^1CHO$ <span style="float:right">(IV),</span>

$R^2CHO$ <span style="float:right">(V)</span> wherein $R^1$ and $R^2$ have the meaning given above, with a compound of general formula (VI),

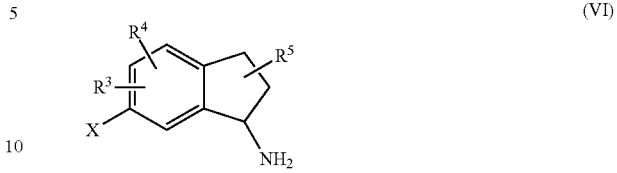

wherein X has the meaning described above. The reductive amination is performed by reaction of a mixture comprising a compound of general formula (IV) or (V), and amino compound of general formula (VI) and a reducing agent in a suitable reaction medium, for a period of time sufficient to achieve the title compound (III). The reductive amination reaction can also be performed under microwave radiation preferably for 5 to 60 minutes, and at a temperature between 90 to 120° C. The use of microwave irradiation limits the formation of undesirable secondary reaction products, compared to what is obtained in a conventional reductive amination procedure.

This process can be performed as a direct reaction when the carbonyl compound of general formula (IV) or (V) and the amine compound of general formula (VI) are mixed with the reducing agent without prior formation of the intermediate imine or iminium salt. A stepwise or indirect reaction involves the reduction of the preformatted imine in a separate step.

Amino compounds of general formula (VI) are obtained by reductive amination with ammonia of carbonyl compounds of general formula (VII), in the conditions described above,

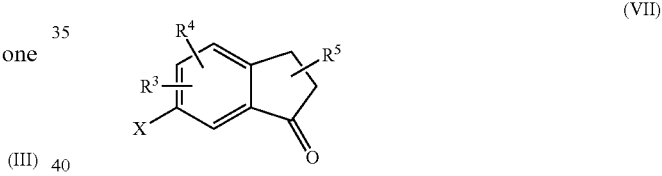

Compounds of general formula (VII) can directly afford compounds of general formula (III) through a reductive amination with secondary amines of general formula (VIII), $HNR^1R^2$ <span style="float:right">(VIII)</span> wherein $R^1$, and $R^2$ have the meaning given above, in the conditions described above.

The choice of the reducing agent for reductive amination reaction can be conventionally made by those skilled in the art. Reducing agents useful in this procedure include hydrogen and a catalyst, zinc and HCl, sodium cyanoborohydride, lithium cyanoborohydride, tetrabutylammonium cyanoborohydride, cyanoborohydride on a solid support, sodium cyanoborohydride and dehydrating agents, sodium cyanoborohydride and titanium additives, sodium cyanoborohydride and zinc halide additives, sodium borohydride, sodium borohydride and dehydrating agents, sodium borohydride and titanium additives, sodium borohydride and zinc salt additives, lithium borohydride, potassium borohydride, polymer-supported borohydride, borohydride exchange resin with nickel acetate or palladium acetate, sodium triacetoxyborohydride, sodium triacetoxyborohydride and additives, tetramethylammonium triacetoxyborohydride, sodium cyano-9-borabicyclo[3.3.1]nonane, lithium triethylborohydride, lithium tri(sec-butyl)borohydride, sodium diisopinocampheylcyanoborohydride, amine boranes, borane-pyridine complex and alkylamine boranes. Sodium triacetoxyborohydride is particularly preferred because is non-toxic and generally does not reduce the carbonyl group prior to imine formation.

The compounds of general formulas (II), (IIa), (IIb), (IIc), (IV), (V), (VII) and (VIII) are either commercially available or can be produced according to methods known to those skilled in the art.

Suitable reaction media are e.g. organic solvents, such as ethers, preferably diethyl ether, dioxane, tetrahydrofurane, dimethyl glycol ether, or alcohols, e.g. methanol, ethanol, propanol, isopropanol, butanol, isobutanol, tert-butanol, or hydrocarbons, preferably benzene, toluene, xylene, hexane, cyclohexane, petroleum ether, or halogenated hydrocarbons, e.g. dichloromethane, trichloromethane, tetrachloromethane, dichloroethylene, trichloroethylene, chlorobenzene or/and other solvents preferably ethyl acetate, triethylamine, pyridine, dimethulsulfoxide, dimethylformamide, hexamethylphosphoramide, acetonitrile, acetone or nitromethane are included. Mixtures based one or more of the above mentioned solvents and water may also be used.

According to the invention, the bases that may be used in the process are generally organic or inorganic bases, preferably alkali metal hydroxides, e.g. sodium hydroxide or potassium hydroxide, or obtained from other metals such as barium hydroxide or different carbonates, preferably potassium carbonate, sodium carbonate, calcium carbonate or alkoxydes, e.g. sodium methoxide potassium methoxide, sodium ethoxide, potassium ethoxide or potassium tert-butoxide, or organic amines, preferably triethylamine, diisopropylethylamine or heterocycles, e.g. 1,4-diazabicyclo[2.2.2]octane, 1,8-diazabicyclo5.4.0]undec-7-ene, pyridine, diamino pyridine, dimethylaminopyridine, methylpiperidine or morpholine. Alkali metals such as sodium or its hydrides, e.g. sodium hydride, may also be used.

The preparation of compounds of general formula (Ia), especially those in which $R^3$, $R^4$ and $R^5$ are all H, is illustrated in scheme 1:

In a further aspect, the present invention also provides an alternative process for the preparation of compounds of general formula (I), according to Scheme 2, especially a process wherein $R^3$, $R^4$ and $R^5$ are all H. According to this process, at least one compound of general formula (IX),

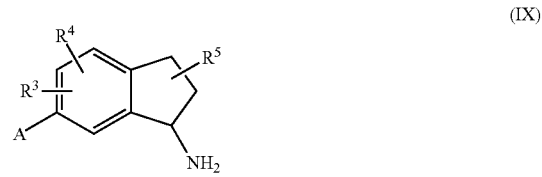

wherein $R^3$, $R^4$, $R^5$ and A have the meaning given above, is subjected to two consecutive reductive amination reaction with aldehydes of general formula (IV) and (V). The reductive amination reaction could be performed following the methods described above.

Amino compounds of general formula (IX) are obtained by reductive amination with ammonia of carbonyl compounds of general formula (X), in the conditions described above,

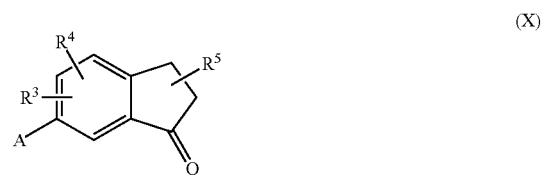

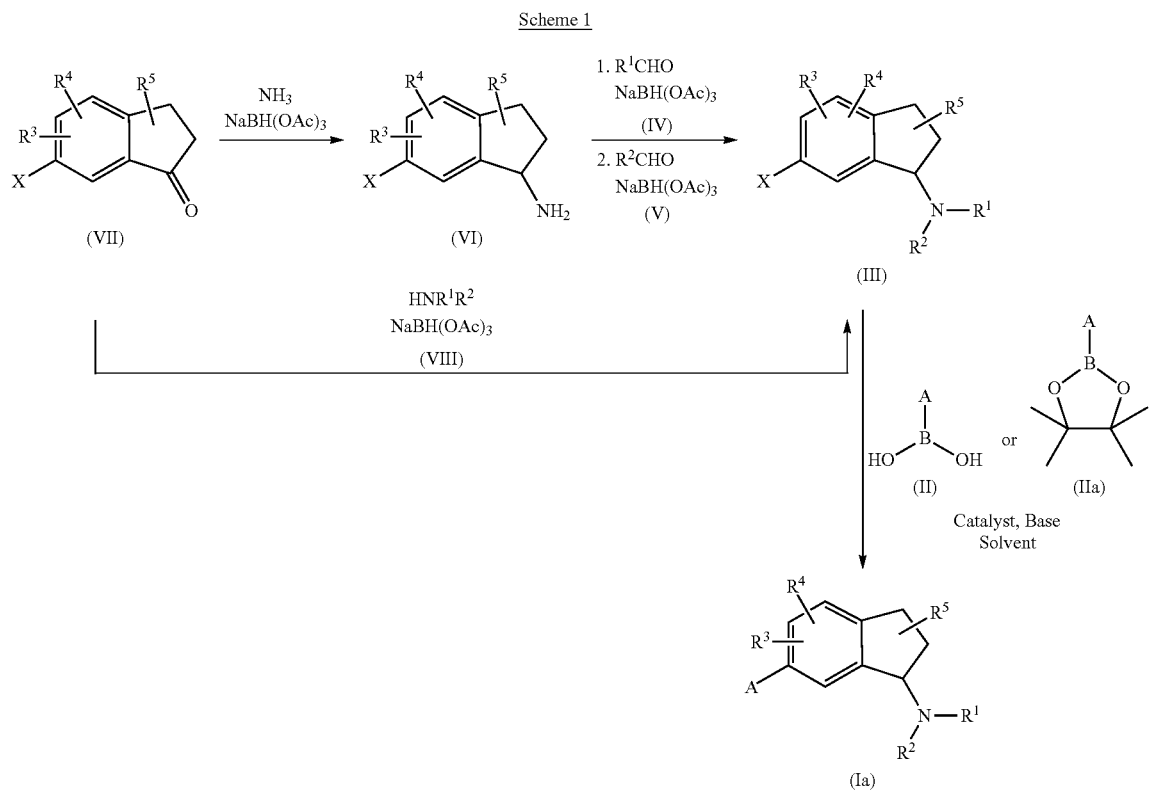

wherein $R^3$, $R^4$, $R^5$, and A have the meaning given above. Compounds of general formula (X) can directly afford compounds of general formula (Ia) through a reductive amination with secondary amines of general formula (VIII), in the conditions described above.

Preparation of compounds of general formula (X) can be achieved by catalytic cross-coupling reactions, which include the Kumada-Corriu-Tamao, Negishi, Stille, Hiyama, Suzuki-Miyaura, Heck, Sonogashira and other cross-coupling reactions known to those skilled in the art. More preferably, the compounds of general formula (X) can be prepared by cross-coupling Suzuki reaction of boronic acids or boronate esters of general formula (II) or (IIa), with at least one compound of general formula (VII). Suzuki reaction could be performed following the methods described above.

This alternative method for the preparation of compounds of general formula (I) is illustrated in scheme 2:

presence of a base and in a suitable reaction medium, with compounds of general formula (IIIb),

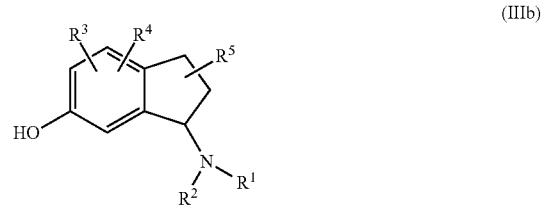

(IIIb)

wherein $R^1$, $R^2$, $R^3$, $R^4$ and $R^5$ have the meaning described above.

Scheme 2

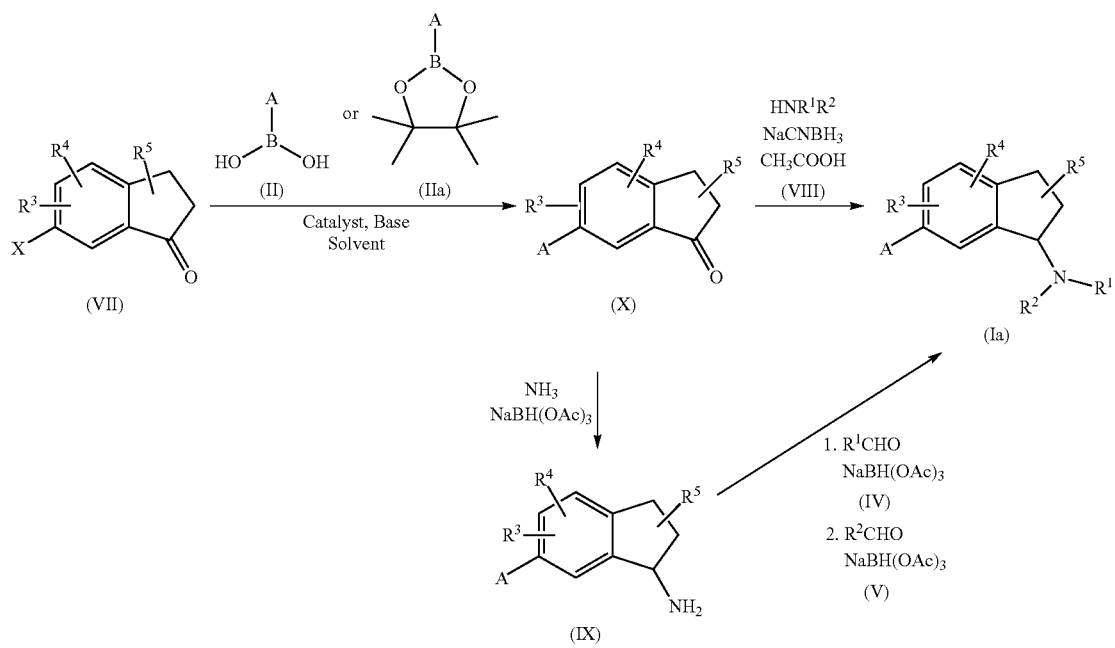

In another aspect, the present invention also provides a process for the preparation of compounds of general formula (Ia), in the particular case in which X is OH, OMe or O-triflate group, according to Scheme 3, especially a process wherein $R^3$, $R^4$ and $R^5$ are all H.

Preparation of compounds of general formula (IIIa),

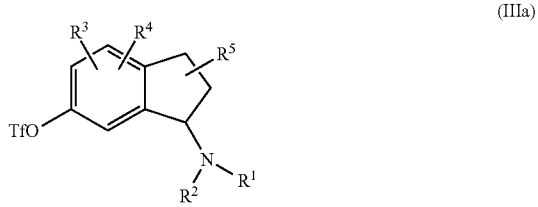

(IIIa)

wherein $R^1$, $R^2$, $R^3$, $R^4$ and $R^5$ have the meaning described above, can be achieved by reaction of triflic anhydride, in the Hydroxyl compounds of general formula (IIIb) are obtained from the methoxy compounds of general formula (IIIc) by heating in HBr 48% at 125° C.,

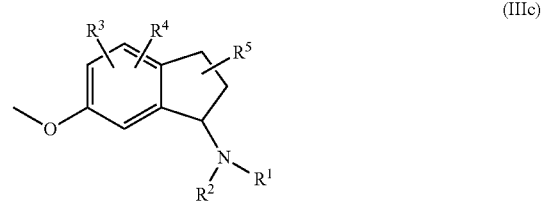

(IIIc)

wherein $R^1$, $R^2$, $R^3$, $R^4$ and $R^5$ have the meaning described above.

Compounds of general formula (IIIc) could be prepared by two consecutive reductive amination reactions from amino compounds of formula (VIa) as described above (Scheme 1). In an alternative synthetic process, compounds of formula (VIIa) can directly afford compounds of general formula (IIIc) through a reductive amination with secondary amines of general formula (VIII).

This alternative method for the preparation of compounds of general formula (I) is illustrated in scheme 3:

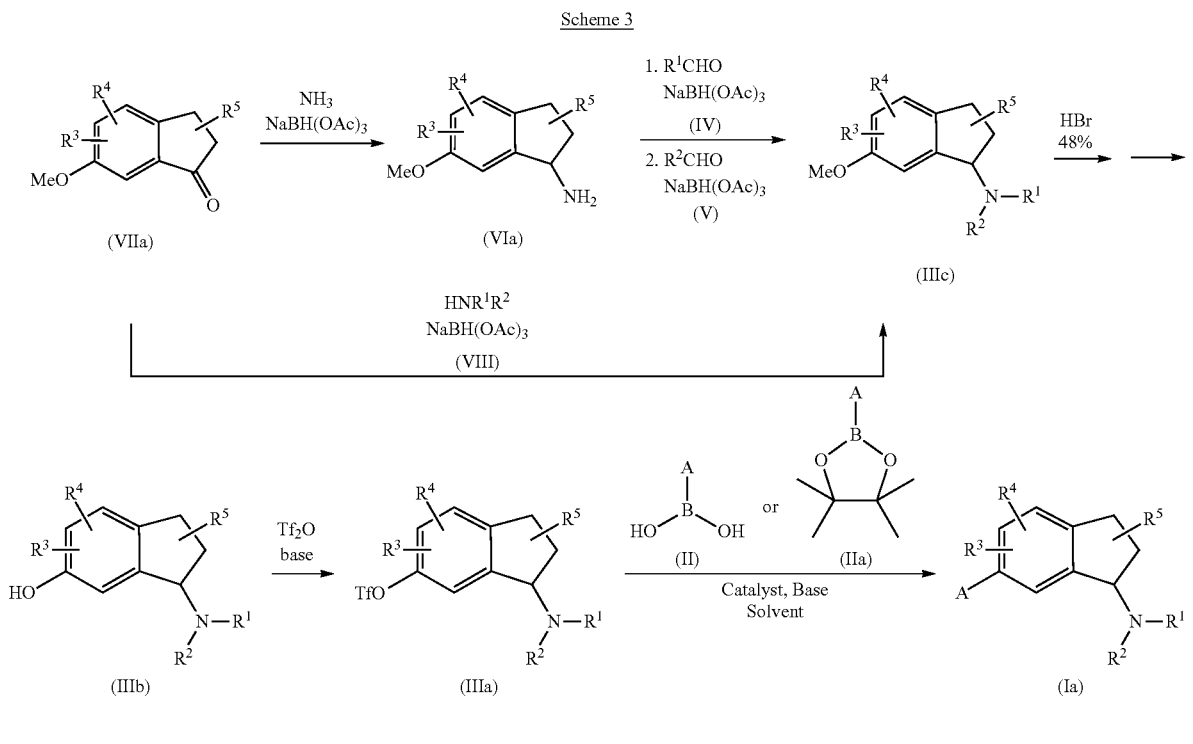

In a further aspect, the present invention also provides an alternative process for the preparation of compounds of general formula (I), according to Scheme 4, especially a process wherein $R^3$, $R^4$ and $R^5$ are all H. According to this process, intermediate compounds of general formula (X) (see Scheme 2), can be achieved by hydrolysis of compounds of general formula (XI),

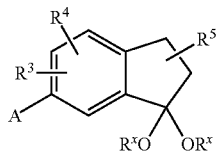 (XI)

wherein A has the meaning given above and $R^x$ being hydrogen or an aliphatic radical, which is linear or branched, saturated or unsaturated, and optionally at least mono-substituted by F, Cl, Br, I, SH or OH. Both $R^x$ together with the bridging oxigen atoms can also form an saturated or unsaturated, optionally at least mono-substituted 5- or 6-membered-heterocyclic ring, which may be condensed with an optionally at least mono-substituted mono- or polycyclic ringsystem.

Preparation of compounds of general formula (XI) can be achieved by catalytic cross-coupling reactions, which include the Kumada-Corriu-Tamao, Negishi, Stille, Hiyama, Suzuki-Miyaura, Heck, Sonogashira and others known to those skilled in the art. More preferably, the compounds of general formula (XI) can be prepared by cross-coupling Suzuki reaction of boronic acids or boronate esters of general formula (II) or (IIa) with at least one compound of general formula (XII),

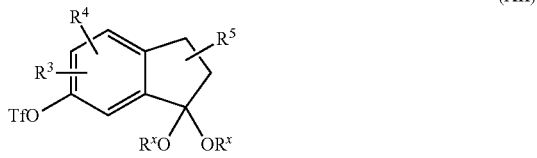 (XII)

wherein $R^3$, $R^4$ and $R^5$ are as described above and $R^x$ has the meaning described above. Suzuki reaction could be performed following the methods described above.

Compounds of general formula (XII) are obtained by reaction of triflic anhydride, in the presence of a base and in a suitable reaction medium, of compounds of general formula (XIII),

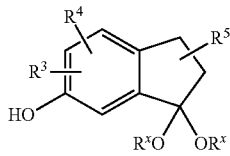 (XIII)

wherein $R^3$, $R^4$, $R^5$ and $R^x$ have the meaning described above.

Hydroxyl compounds of general formula (XIII) are obtained from the methoxy compounds of general formula (XIV) by treatment with $BBr_3$,

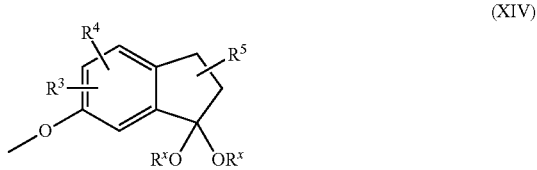 (XIV)

wherein $R^3$, $R^4$, $R^5$ and $R^x$ have the meaning described above. Demethylation reaction could also be performed by other procedures well known to those skilled in the art.

Ketal compounds of general formula (XIV), especially those wherein $R^3$, $R^4$ and $R^5$ are H, could be formed by treatment of carbonyl compounds of formula (VIIa),

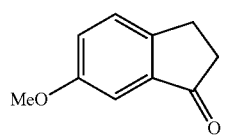

(VIIa)

with an alcohol (R—OH) in the presence of acid catalysts.

The bases that may be used in the process and the suitable reaction media are those described above.

This alternative method for the preparation of compounds of general formula (I) is illustrated in scheme 4:

In another aspect, the present invention also provides an alternative process for the preparation of compounds of general formula (I), according to Scheme 5, wherein $R^1$, $R^2$, $R^3$, $R^4$ and $R^5$ have the meaning given above and A is:

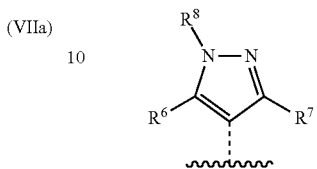

wherein $R^6$, $R^7$ and $R^8$ have the meaning described above, especially a process wherein $R^3$, $R^4$ and $R^5$ are all H.

Scheme 4

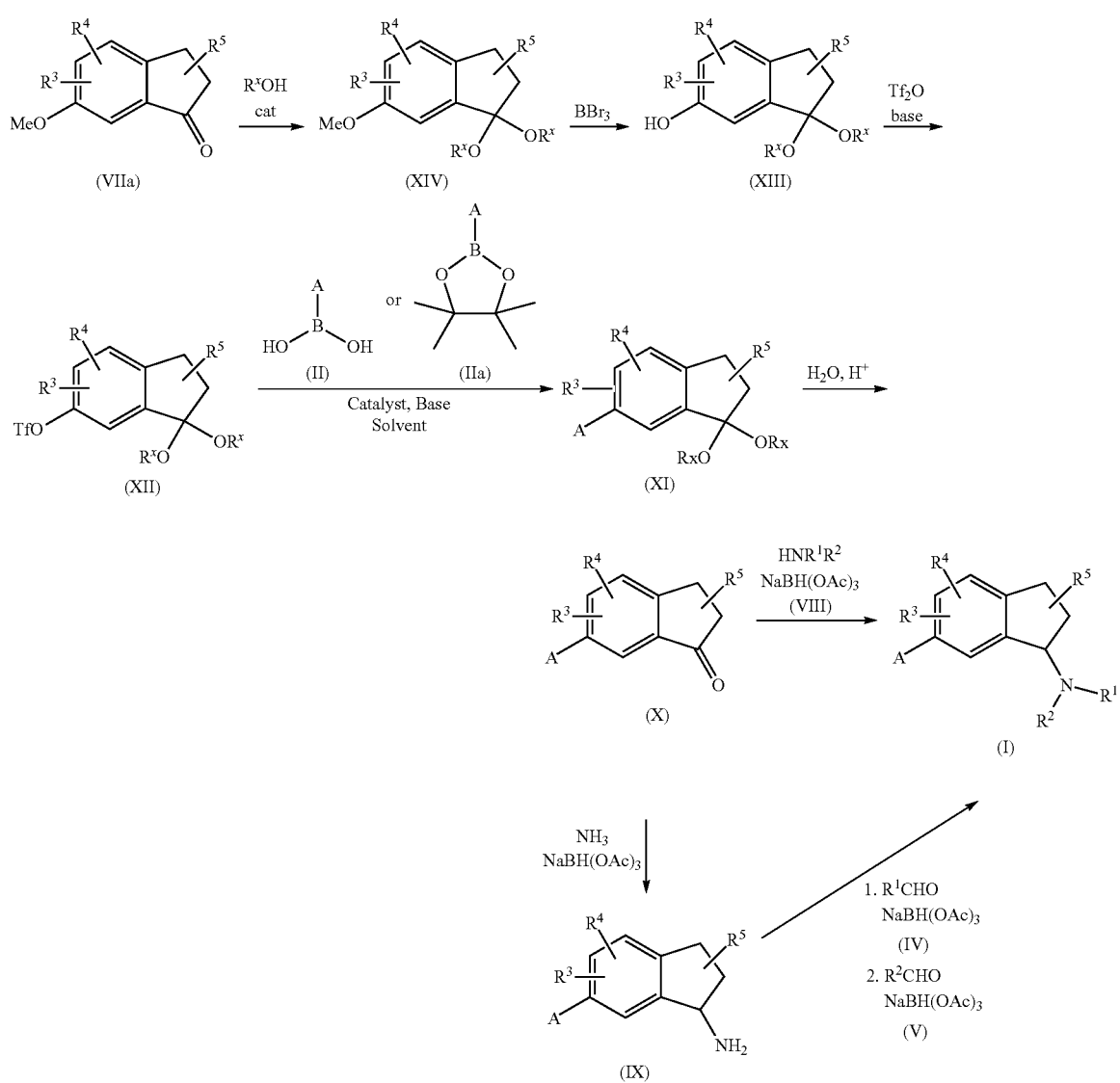

The compounds of general formula (XVI),

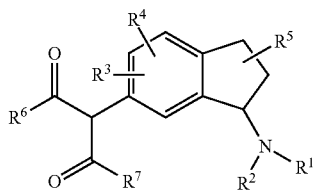
(XVI)

wherein $R^1$, $R^2$, $R^3$, $R^4$, $R^5$, $R^6$ and $R^7$ have the meaning described above were reacted with compounds of general formula (XV),

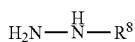
(XV)

wherein $R^8$ have the meaning described above, in a suitable reaction media to give the title compounds of general formula (Ia).

Preparation of compounds of general formula (XVI) can be achieved by copper catalyzed nucleophilic substitution reaction of compounds of general formula (XVII),

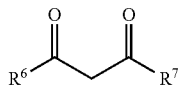
(XVII)

wherein $R^6$ and $R^7$ have the meaning described above, with compounds of general formula (III),

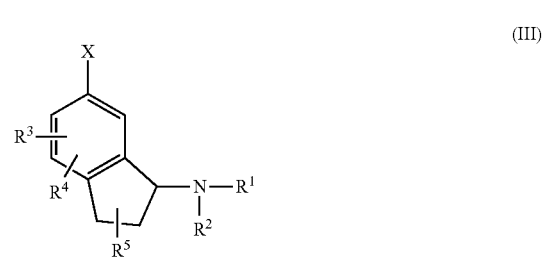
(III)

wherein $R^1$, $R^2$, $R^3$, $R^4$, $R^5$ and X have the meaning described above, in a suitable reaction medium, in the presence of CuX, and at least one base.

Compounds of general formula (III) can be obtained as described above (see Scheme 1).

The compounds of general formulas (IV), (V), (VII), (VIII), (XV) and (XVII) are either commercially available or can be produced according to methods known to those skilled in the art.

Suitable reaction media are those described above.

The bases that may be used in the process are those descried above.

This alternative preparation of compounds of general formula (Ia) is illustrated in scheme 5:

Scheme 5:

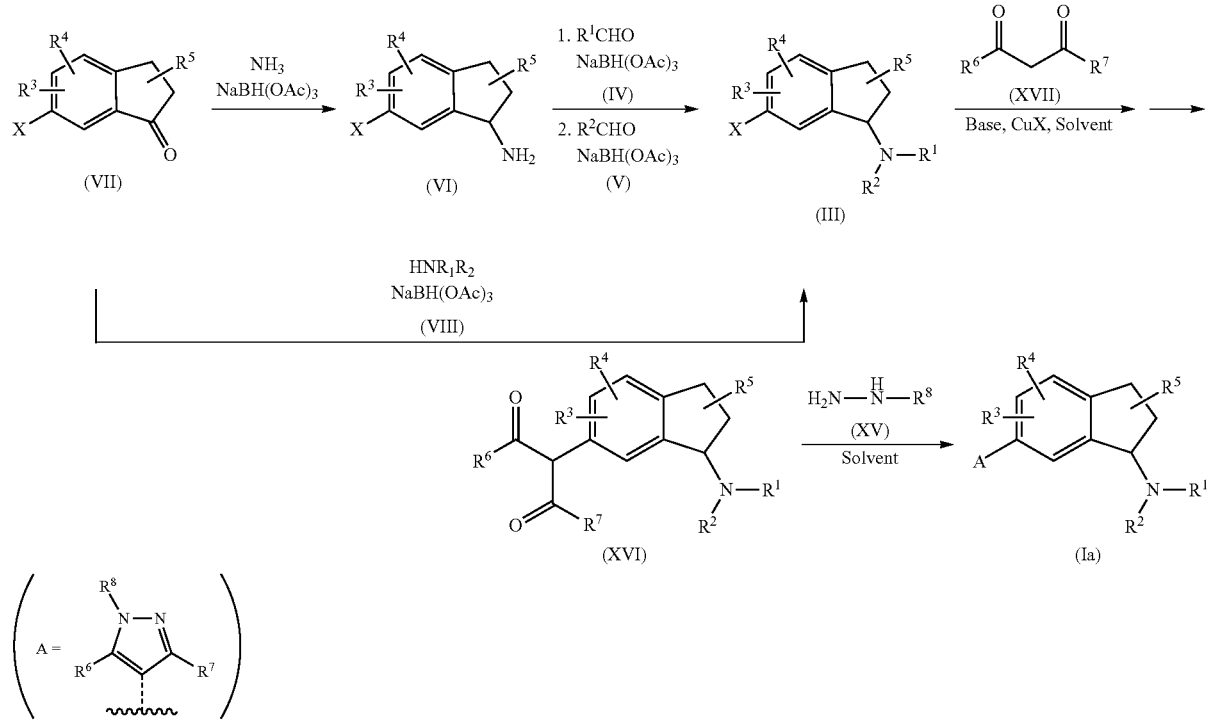

Enantiomerically pure compounds of general formula (S)-(I) or (R)-(I),

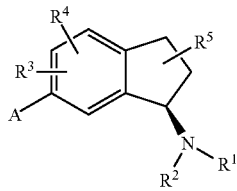
(R)-(Ia)

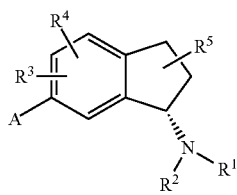
(S)-(Ia)

wherein $R^1$, $R^2$, $R^3$, $R^4$, $R^5$ and A have the meaning given above, are obtained from racemic compounds of general formula (Ia) by standard separation procedures known to those skilled in the art, e.g. chromatographic methods or crystallization with chiral reagents. Compounds of general formula (S)-(Ia) or (R)-(Ia) could also be prepared by enantioselective synthetic methods as for example the one depicted in Scheme 6.

Scheme 6

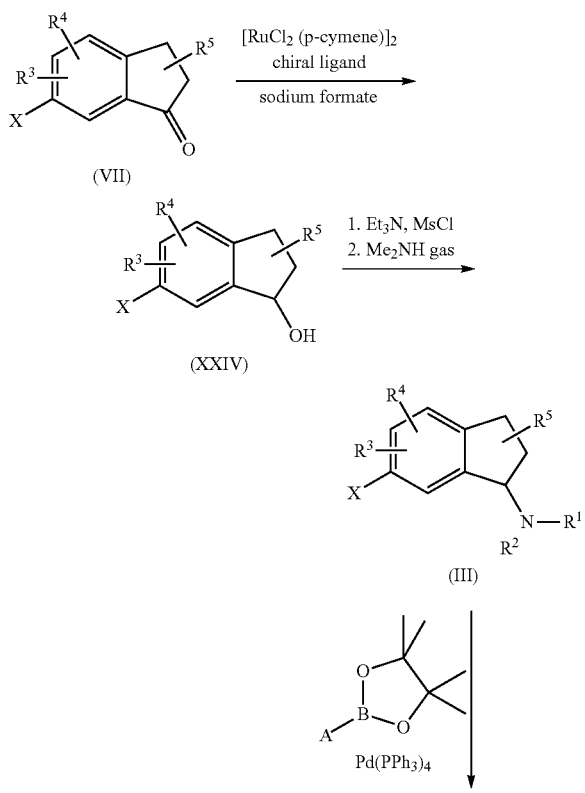

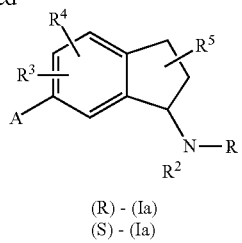
(R) - (Ia)
(S) - (Ia)

Chiral Ligand:
(S, R)-cis aminoindanol
TsDPEN

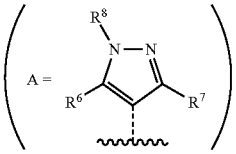

The compounds of general formula (I), or (Ia) their stereoisomers or the respective salts or solvates are toxicologically acceptable and are therefore suitable as pharmaceutical active substances for the preparation of medicaments.

The present invention therefore also provides for a pharmaceutical formulation or medicament comprising at least one compound according to the invention according to formula (I) or formula (Ia), optionally in form of one of its stereoisomers, preferably enantiomers or diastereomers, its racemate or in form of a mixture of at least two of its stereoisomers in any mixing ratio, or a physiologically acceptable salt thereof, or a solvate, respectively, and optionally one or more pharmaceutically acceptable adjuvants.

Furthermore, the present invention also provides for a pharmaceutical composition/medicament comprising at least one compound of general formula (I) or (Ia), optionally in form of one of its stereoisomers, preferably enantiomers or diastereomers, its racemate or in form of a mixture of at least two of its stereoisomers in any mixing ratio, or a physiologically acceptable salt thereof, or a solvate, respectively, and optionally one or more pharmaceutically acceptable adjuvants, which is not yet formulated into a medicament.

Preferably the medicament is suitable for the treatment of a 5-HT$_7$ mediated disease or condition, especially selected from pain, preferably visceral pain, chronic pain, cancer pain, migraine, acute pain or neuropathic pain, more prefearably neuropathic pain, allodynia or hyperalgesia or selected from sleep disorder, shift worker syndrome, jet lag, depression, seasonal affective disorder, migraine, anxiety, psychosis, schizophrenia, cognition and memory disorders, neuronal degeneration resulting from ischemic events, cardiovascular diseases such as hypertension, irritable bowel syndrome, inflammatory bowel disease, spastic colon or urinary incontinence.

The present invention also provides for the use of at least one compound according to formula (I), or (Ia), optionally in form of one of its stereoisomers, preferably enantiomers or diastereomers, its racemate or in form of a mixture of at least two of its stereoisomers in any mixing ratio, or a physiologically acceptable salt thereof, or a solvate, respectively, for the treatment of a 5-HT$_7$ mediated disease or condition. Alternatively it also provides for the use of at least one compound according to formula (I), or (Ia), optionally in form of one of its stereoisomers, preferably enantiomers or diastereomers, its racemate or in form of a mixture of at least two of its stereoisomers in any mixing ratio, or a physiologically acceptable salt thereof, or a solvate, respectively, for the manufacture of a medicament for the treatment of a 5-HT$_7$ mediated disease or condition.

In a preferred embodiment the use according to the invention relates to a use as described above, wherein the disease is pain, preferably visceral pain, chronic pain, cancer pain, migraine, acute pain or neuropathic pain, more prefearably neuropathic pain, allodynia or hyperalgesia.

In another preferred embodiment the use according to the invention relates to a use as described above, wherein the disease is sleep disorder, shift worker syndrome, jet lag, depression, seasonal affective disorder, migraine, anxiety, psychosis, schizophrenia, cognition and memory disorders, neuronal degeneration resulting from ischemic events, cardiovascular diseases such as hypertension, irritable bowel syndrome, inflammatory bowel disease, spastic colon or urinary incontinence.

The medicament/pharmaceutical composition may be in any form suitable for the application to humans and/or animals, preferably mammals, and can be produced by standard procedures known to those skilled in the art. The composition of the medicament may vary depending on the route of administration.

The medicament of the present invention may e.g. be administered parentally in combination with conventional injectable liquid carriers, such as water or suitable alcohols. Conventional pharmaceutical adjuvants for injection, such as stabilizing agents, solubilizing agents, and buffers, may be included in such injectable compositions. These medicaments may preferably be injected intramuscularly, intraperitoneally, or intravenously.

Medicaments according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, pellets, capsules, lozenges, aqueous or oily solutions, suspensions, emulsions, or dry powdered form suitable for reconstitution with water or other suitable liquid medium before use, for immediate or controlled release.

The liquid oral forms for administration may also contain certain additives such as sweeteners, flavoring, preservatives, and emulsifying agents. Non-aqueous liquid compositions for oral administration may also be formulated, containing e.g. edible oils. Such liquid compositions may be conveniently encapsulated in e.g., gelatin capsules in a unit dosage amount.

The compositions of the present invention may also be administered topically or via a suppository.

The above mentioned compositions include preferably 1 to 60% by weight of one or more of the compound of general formula (I), optionally in form of one of its stereoisomers, preferably enantiomers or diastereomers, its racemate or in form of a mixture of at least two of its stereoisomers in any mixing ratio, or a physiologically acceptable salt thereof, or a solvate, respectively, and 40 to 99% by weight of the appropriate pharmaceutical vehicle(s).

The daily dosage for humans and animals may vary depending on factors that have their basis in the respective species or other factors, such as age, weight or degree of illness and so forth. The daily dosage for mammals including humans usually ranges from 1 milligram to 2000 milligram, preferably 1 to 1500 mg, more preferably 1 to 1000 mg of substance to be administered during one or several intakes.

Thus, the invention also provides a method of treatment for an animal or human in need thereof using the medicament/pharmaceutical compositions described above.

Pharmacological Methods:
Radioligand Binding

Radioligand binding assays were performed using the Cloned Human Serotonin Receptor, Subtype 7 (h5HT$_7$), expressed in CHO cells, coated on Flashplate (Basic FlashPlate Cat.: SMP200) from PerkinElmer (Cat.: 6120512). The protocol assay was essentially the recommended protocol in the Technical Data Sheet by PerkinEmer Life and Analytical Sciences. The Mass membrane protein/well was typically 12 µg and the Receptor/well was about 9-10 fmoles. The Flashplate were let equilibrate at room temperature for one hour before the addition of the components of the assay mixture. The binding buffer was: 50 mM Tris-HCl, pH 7.4, containing 10 mM MgCl$_2$, 0.5 mM EDTA and 0.5% BSA. The radioligand was [$^{125}$I]LSD at a final concentration of 0.82 nM. Nonspecific binding was determined with 50 µM of Clozapine. The assay volume was 25 µl. TopSeal-A were applied onto Flashplate microplates and they were incubated at room temperature for 240 minutes in darkness. The radioactivity were quantified by liquid scintillation spectrophotometry (Wallac 1450 Microbeta Trilux) with a count delay of 4 minutes prior to counting and a counting time of 30 seconds per well. Competition binding data were analyzed by using the LIGAND program (Munson and Rodbard, LIGAND: A versatile, computerized approach for characterization of ligand-binding systems. *Anal. Biochem.* 107: 220-239, 1980) and assays were performed in triplicate determinations for each point.

Functionality assay on the 5HT7 receptor were done according to those known in the state of the art.

The following figures and examples are given to illustrate the present invention, but they do not limit the scope of the present invention.

FIGURES

FIG. 1) X-Ray of the crystal structure of example 1 (Ortep-Plot (50%) with labeling scheme)

FIG. 2) X-Ray of the crystal structure of example 1 (Ortep-Plot (50%))

FIGS. 1 and 2 show the crystal structure of Example 1 (see below) by X-Ray. The experimental preparation of the X-Ray analysis is also described below.

EXAMPLES

Example A (of Compounds of General Formula (III))

(6-Bromo-indan-1-yl)-dimethyl-amine

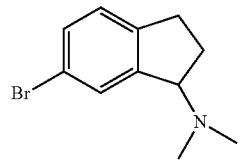

(Method 1): 6-Bromo-indan-1-one (0.23 mmol) and dimethyl-amine (0.71 mmol) were mixed in 3 ml of 1,2-dichloroethane in a process vial, which was sealed with a septum. Sodium triacetoxyborohydride (0.47 mmol) was added under argon atmosphere. The suspension was subjected to microwave irradiating conditions (CEM Discover® equipped with a CEM Explorer® automated reaction handling module). The reaction mixture was heated for 5 min at 120° C. and then cooled. The crude was evaporated to dryness and then suspended in aqueous NaHCO₃ The product was extracted with CH₂Cl₂ and washed with aqueous NaHCO₃. The CH₂Cl₂ extract was dried with anhydrous Na₂SO₄, filtered and evaporated to dryness to give the crude product (6-bromo-indan-1-yl)-dimethyl-amine. The crude was purified by flash column chromatography (CH₂Cl₂-MeOH as eluents) by using a CombiFlash Companion™ system to yield the title compound (85%). MS [MH]⁺=240.

(Method 2): 6-Bromo-indan-1-one (0.58 mmol) was dissolved in MeOH. Dimethyl-amine (3.7 mmol), acetic acid (0.059 mmol) and sodium cyanoborohydride (1.74 mmol) were added under argon atmosphere. The suspension was refluxed overnight and then cooled. The crude was evaporated to dryness and then suspended in water. The product was extracted with CH₂Cl₂ and washed with water. The CH₂Cl₂ extract was dried with anhydrous Na₂SO₄, filtered and evaporated to dryness to give the crude product (6-bromo-indan-1-yl)-dimethyl-amine (80% conversion LC-MS). The crude product was used in the next synthetic step (Suzuki coupling), without further purification.

Example B (of Compounds of General Formula (X))

6-(1,3,5-Trimethyl-1H-pyrazol-4-yl)-indan-1-one

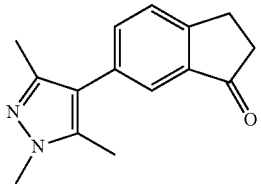

6-Bromo-indan-1-one (0.94 mmol) was dissolved in DME/H₂O 1/1 (10 mL) under argon atmosphere. 1,3,5-Trimethyl-1H-pyrazole-4-boronic acid pinacol ester (1.42 mmol), K₂CO₃ (2.82 mmol), and tetrakis-(triphenylphosphine)palladium (5 mol %, 0.047 mmol) were added and the reaction mixture was stirred at 100° C. for 3 h. The reaction mixture was evaporated to dryness, then dissolved in CHCl₃ and filtered through Celite® to give the crude product 6-(1,3,5-trimethyl-1H-pyrazol-4-yl)-indan-1-one. The crude was purified by flash column chromatography (AcOEt-Cyclohexane as eluents) by using a CombiFlash Companion™ system to yield the title compound (84%). MS [MH]⁺=240

Example 1

Dimethyl-[6-(1,3,5-trimethyl-1H-pyrazol-4-yl)-indan-1-yl]-amine dihydrochloride

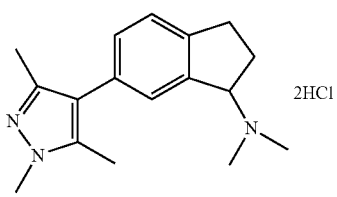

(Method 1): 6-(1,3,5-Trimethyl-1H-pyrazol-4-yl)-indan-1-one (0.20 mmol), dimethyl-amine (2.31 mmol) and acetic acid (0.020 mmol) were mixed in 3 ml of MeOH in a process vial, which was sealed with a septum. Sodium cyanoborohydride (0.47 mmol) was added under argon atmosphere. The suspension was subjected to microwave irradiating conditions (CEM Discover® equipped with a CEM Explorer® automated reaction handling module). The reaction mixture was heated for 1 h at 120° C. and then cooled. The crude was evaporated to dryness and then suspended in water. The product was extracted with CH₂Cl₂ and washed with water. The CH₂Cl₂ extract was dried with anhydrous Na₂SO₄, filtered and evaporated to dryness to give the crude product dimethyl-[6-(1,3,5-trimethyl-1H-pyrazol-4-yl)-indan-1-yl]-amine.

The crude was purified by flash column chromatography (CH₂Cl₂-MeOH as eluents) by using a CombiFlash Companion™ system to yield the base of the title compound. The obtained product was diluted in ethyl acetate (5 mL) and a solution of hydrogen chloride 2,0 M in diethylether was added. The resulting precipitate was filtered and dried under vacuum to yield the title compound dimethyl-[6-(1,3,5-trimethyl-1H-pyrazol-4-yl)-indan-1-yl]-amine dihydrochloride (83%). MS [MH]⁺=270.

(Method 2): 6-(1,3,5-Trimethyl-1H-pyrazol-4-yl)-indan-1-one (1.1 mmol) was dissolved in MeOH. Dimethyl-amine (24.5 mmol), acetic acid (0.11 mmol) and sodium cyanoborohydride (2.2 mmol) were added under argon atmosphere. The suspension was refluxed overnight and then cooled. The crude was evaporated to dryness and then suspended in water. The product was extracted with CH₂Cl₂ and washed with water. The CH₂Cl₂ extract was dried with anhydrous Na₂SO₄, filtered and evaporated to dryness to give the crude product dimethyl-[6-(1,3,5-trimethyl-1H-pyrazol-4-yl)-indan-1-yl]-amine. The crude was purified by flash column chromatography (CH₂Cl₂-MeOH as eluents) by using a CombiFlash Companion™ system to yield the base of the title compound. The obtained product was diluted in ethyl acetate and a solution of hydrogen chloride 2.0 M in diethylether was added. The resulting precipitate was filtered and dried under vacuum to yield the title compound dimethyl-[6-(1,3,5-trimethyl-1H-pyrazol-4-yl)-indan-1-yl]-amine dihydrochloride (79%). MS [MH]⁺=270.

(Method 3): (6-Bromo-indan-1-yl)-dimethyl-amine (0.82 mmol) was dissolved in DME/H₂O 1/1 (10 mL) under argon atmosphere. 1,3,5-Trimethyl-1H-pyrazole-4-boronic acid pinacol ester (0.82 mmol), K₂CO₃ (3.08 mmol), and tetrakis-(triphenylphosphine)palladium (3 mol %, 0.025 mmol) were added and the reaction mixture was stirred at 100° C. for 3 h. Then, a second fraction of 1,3,5-trimethyl-1H-pyrazole-4-boronic acid pinacol ester (0.41 mmol) was added and the reaction mixture was stirred at 100° C. for 2 h more. The reaction mixture was evaporated to dryness, then dissolved in CHCl₃ and filtered through Celite® to give the crude product dimethyl-[6-(1,3,5-trimethyl-1H-pyrazol-4-yl)-indan-1-yl]-amine. The crude was purified by flash column chromatography (CH₂Cl₂ and MeOH as eluents) by using a CombiFlash Companion™ system to yield the base of the title compound. The obtained product was diluted in ethyl acetate and a solution of hydrogen chloride 2.0 M in diethylether was added. The resulting precipitate was filtered and dried under vacuum to yield the title compound dimethyl-[6-(1,3,5-trimethyl-1H-pyrazol-4-yl)-indan-1-yl]-amine dihydrochloride (75%). MS [MH]⁺=270.

Examples 2 and 3

Through Separation on a Chiral HPLC Column

Enantiomers of dimethyl-[6-(1,3,5-trimethyl-1H-pyrazol-4-yl)-indan-1-yl]-amine Enantiomers of Example 1 (dimethyl-[6-(1,3,5-trimethyl-1H-pyrazol-4-yl)-indan-1-yl]-amine) were—in one option—obtained by separation on a chiral HPLC column (Chiralpak AD-H 4.6×250 mm, 5 μm). The mobile phase was heptane/EtOH 98/2 v/v+0.1% DEA.

Tr(enantiomer R)=29.3 min $[\alpha]_D^{20}$=−72.17 (c=1, MeOH)

Tr(enantiomer S)=37.8 min $[\alpha]_D^{20}$=+70.29 (c=1, MeOH)

Example of Compounds of General Formula (XXIV)

(S)-6-Bromo-indan-1-ol

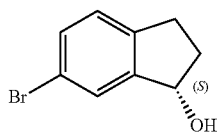

[RuCl$_2$(p-cymene)]$_2$ (0.005 mmol) and (1S,2S)—N-p-Tosyl-diphenylethylenediamine (0.012 mmol) were suspended in 2 mL of water. The system was degassed (an argon flow was passed through the solution) and heated at 70° C. for 1.5 h. 6-Bromo-1-indanone (1 mmol) and sodium formate (5 mmol) were added, the system was degassed again and previously degassed THF (0.8 mL) was added. The reaction mixture was stirred at 40° C. under Ar atmosphere until starting material could not be detected by TLC (20 h). The reaction mixture was cooled to room temperature and extracted with EtOAc. The combined organic layers were washed with brine, dried over anhydrous MgSO$_4$ and concentrated in vacuo. Crude was then filtered through a pad of SiO$_2$ using cyclohexane/EtOAc as eluent. The product was obtained as a white solid. Then, 6-bromo-indan-1-ol was recrystallised from cyclohexane to obtain pure product in 67% overall yield and 99.9% ee.

$^1$H-NMR (400 MHz, CDCl$_3$): δ ppm 7.3-7.2 (m, 2H), 7.14 (dd, 1H, J 8 and 2 Hz), 5.26 (t, 1H, J=6 Hz), 3.09-3.01 (m, 1H), 2.87-2.80 (m, 1H), 2.62-2.54 (m, 1H), 2.03-1.96 (m 1H).

HPLC. Chiralpack IA. Heptane:IPA 95:5, 0.5 mL/min, λ=220 nm, $t_R$ (S)=18.8 min, $t_R$ (R)=22.7 min.

Example of Compounds of General Formula (R)-(III)

(R)-(6-Bromo-indan-1-yl)-dimethyl-amine

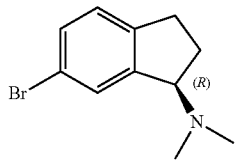

A solution of (S)-6-bromo-indan-1-ol (1 mmol) and NEt$_3$ (4 mmol) in dry THF (5 mL) was stirred at −15° C. under argon. A solution of methanesulfonyl chloride (2 mmol) in dry THF (1 mL) was cooled to −78° C. and then added slowly to the alcohol solution maintaining the temperature below 0° C. The reaction mixture was stirred for 2 h at −15° C. and then purged with dimethylamine gas (12 mmol). The reaction mixture was allowed to warm to room temperature and stirred overnight. Then, it was filtered to remove salts and solvent was evaporated. Crude was used in next step without further purification.

$^1$H-NMR (400 MHz, CDCl$_3$): δ ppm 7.49 (s, 1H), 7.32 (dd, 1H, J 8 and 2 Hz), 7.07 (d, 1H, J=8 Hz), 4.30 (t, 1H, J=7 Hz), 2.91-2.83 (m, 1H), 2.79-2.71 (m, 1H), 2.25 (s, 6H), 2.09-2.03 (m 2H).

Example 2

Base Compound

(R)-Dimethyl-[6-(1,3,5-trimethyl-1H-pyrazol-4-yl)-indan-1-yl]-amine

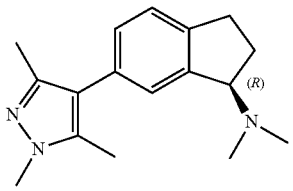

(Method 1): To a solution of K$_2$CO$_3$ (1.9 mmol) and (R)-(6-bromo-indan-1-yl)-dimethyl-amine (1 mmol) in 1,2-dimethoxyethane (8.8 mL)/water (1.2 mL) was added Pd(PPh$_3$)$_4$ (0.1 mmol) and 1,3,5-trimethyl-1H-pyrazole-4-boronic acid pinacol ester (1.2 mmol). The reaction mixture was degassed and stirred at 85° C. for 6 h. The solvent was evaporated, crude was redissolved in dichloromethane and filtered through a pad of Celite. The filtrate was extracted with 6M HCl (3×0.16 mL). The aqueous layer was basified with 6M NaOH to pH 13 and extracted with dichloromethane. The combined organic extracts were dried over anhydrous Na$_2$SO$_4$, filtered and concentrated in vacuo. Crude was purified by flash chromatography (CH$_2$Cl$_2$-MeOH-NEt$_3$ as eluents) to yield (1R)-dimethyl-[6-(1,3,5-trimethyl-1H-pyrazol-4-yl)-indan-1-yl]-amine as an oil (52% yield). Product was obtained with a final ee of 99.6% (determined by chiral HPLC).

$^1$H-NMR (400 MHz, CDCl$_3$): δ ppm 7.78 (s, 1H), 7.53 (d, 1H, J=8 Hz), 7.44 (d, 1H, J=8 Hz), 5.10-5.15 (m, 1H), 4.04 (s, 3H), 3.27-3.21 (m, 1H), 3.14-3.05 (m, 1H), 2.94 (s, 3H), 2.68 (s, 3H), 2.64-2.48 (m, 2H), 2.43 (s, 6H).

HPLC. Chiralpack AD-H. n-heptane:EtOH:DEA 98:2:0.1, 0.5 mL/min, λ=220 nm, $t_R$ (R)=29 min, $[\alpha]_{D,RT}$=−72.17° (C=1, MeOH)

(Method 2, Crystallization with L-di-p-toluiltartaric Acid):

Step 1: (R)-Dimethyl-[6-(1,3,5-trimethyl-1H-pyrazol-4-yl)-indan-1-yl]-amine (−)-di-O,O'-p-toluoyl-L-tartaric acid salt

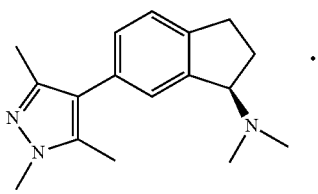

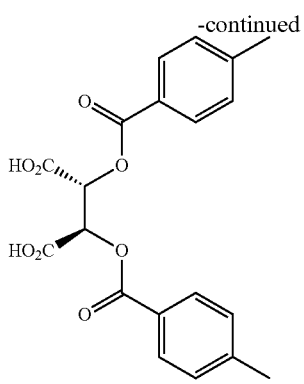

L-di-p-toluiltartaric acid (16.62 mmol) was dropwise added to a solution of dimethyl-[6-(1,3,5-trimethyl-1H-pyrazol-4-yl)-indan-1-yl]-amine (15.11 mmol) in refluxing acetone (30 mL). The reflux temperature was maintained for 30 min and then the reaction was allowed to reach 25° C. very slowly (27 h). The mixture was cooled to 20° C. and stirred for 1 h. Then, 15 mL of acetone were added and the suspension was stirred at 20° C. for 1 h more. The salt formed was collected by filtration, washed with acetone (3×10 mL) and vacuum dried, to give a white solid (72.98% ee, determined by chiral HPLC). The obtained solid was suspended in acetone (130 mL) and EtOH (70 mL) and submitted to reflux until complete dissolution. Refluxing temperature was kept for 40 min and then the reaction was allowed to reach 20° C. very slowly (16 h). The mixture was cooled to −10° C. and stirred for 7.5 h. The obtained diastereomeric salt was filtered, washed with acetone (3×10 mL) and vacuum dried, to yield a white solid (98.48% ee, determined by chiral HPLC, 22% yield).

$^1$H-RMN (250 MHz DMSO-$d_6$) δ ppm 7.80 (d, 4H, J=8.2 Hz), 7.32 (m, 7H), 5.65 (s, 2H), 4.80 (m, 1H), 3.68 (s, 3H), 3.00-2.75 (m, 2H), 2.49 (s, 6H), 2.35 (s, 6H), 2.27 (m, 2H), 2.19 (s, 3H), 2.11 (s, 3H).

HPLC. ChiralPak IC. 2-PrOH:Hexane:DEA 5:95:0.1, 1 mL/min.

Step 2: (R)-Dimethyl-[6-(1,3,5-trimethyl-1H-pyrazol-4-yl)-indan-1-yl]-amine

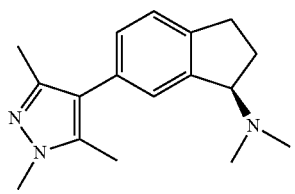

NaOH 10% (100 mL) was added to a suspension of (R)-dimethyl-[6-(1,3,5-trimethyl-1H-pyrazol-4-yl)-indan-1-yl]-amine (−)-di-O,O′-p-toluoyl-L-tartaric acid salt (2.96 mmol) in ethyl acetate (80 mL). The mixture was stirred at room temperature for 30 minutes. The organic layer was washed with NaOH 10% (2×100 mL) and water (1×100 mL) and finally dried over anhydrous Na$_2$SO$_4$, filtered and concentrated in vacuo to yield the target compound (1R)-dimethyl-[6-(1,3,5-trimethyl-1H-pyrazol-4-yl)-indan-1-yl]-amine as an oil (97% yield). Product was obtained with a final ee of 98.48% (determined by chiral HPLC).

Example 2

Hydrochloride Salt (R)-Dimethyl-[6-(1,3,5-trimethyl-1H-pyrazol-4-yl)-indan-1-yl]-amine hydrochloride

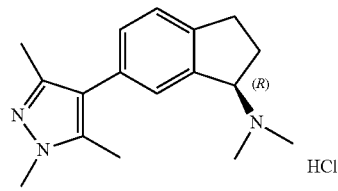

HCl (0.9 mmol, 2 M solution in Et$_2$O) was dropwise added to a solution of (R)-dimethyl-[6-(1,3,5-trimethyl-1H-pyrazol-4-yl)-indan-1-yl]-amine (1 mmol) in ethyl acetate. The reaction mixture was stirred at room temperature for 30 min and then the solvent was concentrated off. The resulting solid was suspended in acetone and the precipitate formed was collected by filtration, washed with acetone and vacuum dried, giving the title compound as a white solid (75%).

Example 2

Dihydrochloride Salt (R)-Dimethyl-[6-(1,3,5-trimethyl-1H-pyrazol-4-yl)-indan-1-yl]-amine dihydrochloride

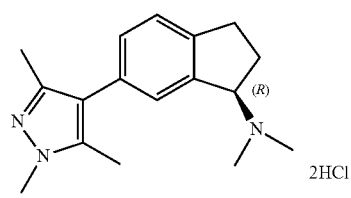

HCl (2.1 mmol, 2 M solution in Et$_2$O) was dropwise added to a solution of (R)-dimethyl-[6-(1,3,5-trimethyl-1H-pyrazol-4-yl)-indan-1-yl]-amine (1 mmol) in ethyl acetate. The reaction mixture was stirred at room temperature for 30 min and then the solvent was concentrated off. The resulting solid was suspended in Et$_2$O and concentrated, in order to remove excess of HCl. This operation was done for three times, to give the title product (white solid, 98% yield).

EXAMPLES 1 to 42 were or are prepared according or analogously to Example 1 or using the Reaction Schemes 1 to 6 given above. Examples are depicted in the following table.

| Example | Structure | Name | ¹H-NMR | MS (APCI (M+H)⁺) |
|---|---|---|---|---|
| 1 | 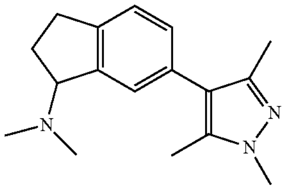 | Dimethyl-[6-(1,3,5-trimethyl-1H-pyrazol-4-yl)-indan-1-yl]-amine | 1H NMR (300 MHz, METHANOL-d₄) δ ppm 2.29 (s, 3H) 2.33 (s, 3H) 2.45-2.61 (m, 2H) 2.68 (s, 3H) 2.92 (s, 3H) 3.07-3.16 (m, 1H) 3.17-3.28 (m, 1H) 4.00 (s, 3H) 5.10 (d, J = 4.69 Hz, 1H) 7.42 (d, J = 7.76 Hz, 1H) 7.55 (d, J = 7.62 Hz, 1H) 7.72 (s, 1H) (dihydrochloride product) | 270 |
| 2 | 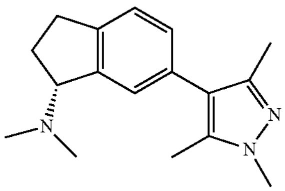 | (R) Dimethyl-[6-(1,3,5-trimethyl-1H-pyrazol-4-yl)-indan-1-yl]-amine | 1H NMR (300 MHz, METHANOL-d₄) δ ppm 2.29 (s, 3H) 2.33 (s, 3H) 2.45-2.61 (m, 2H) 2.68 (s, 3H) 2.92 (s, 3H) 3.07-3.16 (m, 1H) 3.17-3.28 (m, 1H) 4.00 (s, 3H) 5.10 (d, J = 4.69 Hz, 1H) 7.42 (d, J = 7.76 Hz, 1H) 7.55 (d, J = 7.62 Hz, 1H) 7.72 (s, 1H) (hydrochloride product) | 270 |
| 3 | 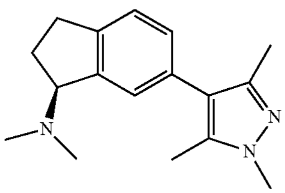 | (S) Dimethyl-[6-(1,3,5-trimethyl-1H-pyrazol-4-yl)-indan-1-yl]-amine | 1H NMR (300 MHz, METHANOL-d₄) δ ppm 2.29 (s, 3H) 2.33 (s, 3H) 2.45-2.61 (m, 2H) 2.68 (s, 3H) 2.92 (s, 3H) 3.07-3.16 (m, 1H) 3.17-3.28 (m, 1H) 4.00 (s, 3H) 5.10 (d, J = 4.69 Hz, 1H) 7.42 (d, J = 7.76 Hz, 1H) 7.55 (d, J = 7.62 Hz, 1H) 7.72 (s, 1H) (hydrochloride product) | 270 |
| 4 | 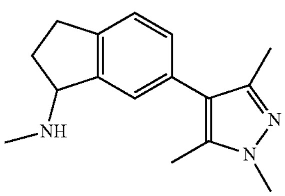 | Methyl-[6-(1,3,5-trimethyl-1H-pyrazol-4-yl)-indan-1-yl]-amine | 1H NMR (400 MHz, CHLOROFORM-d) δ ppm 1.94-2.01 (m, 1H) 2.24 (s, 6H) 2.39-2.50 (m, 1H) 2.52 (s, 3H) 2.83-2.92 (m, 1H) 3.02-3.11 (m, 1H) 3.77 (s, 3H) 4.29 (t, J = 6.45 Hz, 1H) 7.11 (d, J = 7.82 Hz, 1H) 7.28 (m, 2H) | 256 |
| 5 | 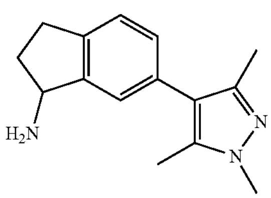 | 6-(1,3,5-Trimethyl-1H-pyrazol-4-yl)-indan-1-ylamine | | 242 |
| 6 | 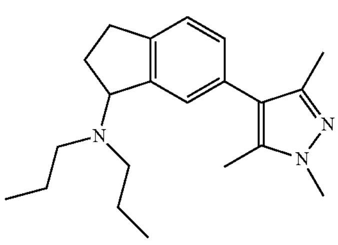 | Diethyl-[6-(1,3,5-trimethyl-1H-pyrazol-4-yl)-indan-1-yl]-amine | 1H NMR (300 MHz, METHANOL-d₄) δ ppm 1.32 (t, J = 7.25 Hz, 3H) 1.48 (t, J = 7.25 Hz, 3H) 2.38 (s, 3H) 2.40 (s, 3H) 2.40-2.49 (m, 1H) 2.50-2.68 (m, 1H) 2.96-3.25 (m, 5H) 3.36-3.47 (m, 1H) 3.98 (s, 3H) 5.30 (dd, J = 8.57, 4.47 Hz, 1H) 7.41 (d, J = 7.91 Hz, 1H) 7.54 (d, J = 7.76 Hz, 1H) 7.73 (s, 1H) (hydrochloride product) | 298 |
| 7 | 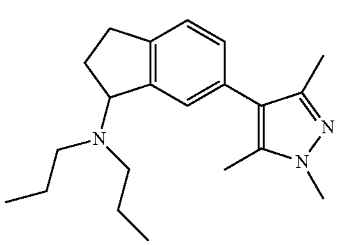 | Dipropyl-[6-(1,3,5-trimethyl-1H-pyrazol-4-yl)-indan-1-yl]-amine | 1H NMR (300 MHz, METHANOL-d₄) δ ppm 0.87 (t, J = 7.40 Hz, 6H) 1.43-1.65 (m, 4H) 1.96-2.10 (m, 1H) 2.16 (s, 3H) 2.19 (m, 1H) 2.23 (s, 3H) 2.32-2.53 (m, 4H) 2.72-3.01 (m, 2H) 3.76 (s, 3H) 4.58 (t, J = 7.47 Hz, 1H) 7.06 (d, J = 7.62 Hz, 1H) 7.18-7.28 (m, 2H) | 326 |

| Example | Structure | Name | ¹H-NMR | MS (APCI (M +H)⁺) |
|---|---|---|---|---|
| 8 | 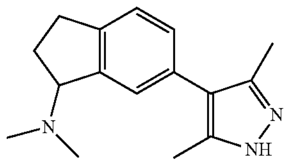 | [6-(3,5-Dimethyl-1H-indan-1-yl]-dimethyl-amine | 1H NMR (300 MHz, METHANOL-d₄) δ ppm 2.16-2.22 (m, 2H) 2.24 (s, 6H) 2.34 (s, 6H) 2.78-2.95 (m, 1H) 2.95-3.11 (m, 1H) 4.46 (t, J = 6.45 Hz, 1H) 7.18 (dd, J = 7.76, 1.32 Hz, 1H) 7.31 (m, 2H) (dihydrochloride product) | 256 |
| 9 | 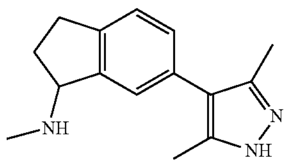 | [6-(3,5-Dimethyl-1H-pyrazol-4-yl)-indan-1-yl]-methyl-amine | 1H NMR (300 MHz, METHANOL-d₄) δ ppm 2.17-2.36 (m, 1H) 2.43 (s, 6H) 2.65 (td, J = 14.72, 7.91 Hz, 1H) 2.78 (s, 3H) 3.01-3.17 (m, 1H) 3.18-3.27 (m, 1H) 4.83 (m, 1H) 7.42 (d, J = 7.91 Hz, 1H) 7.47-7.57 (m, 1H) 7.65 (s, 1H) (dihydrochloride product) | 242 |
| 10 | 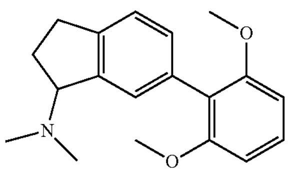 | [6-(2,6-Dimethoxy-phenyl)-indan-1-yl]-dimethyl-amine | 1H NMR (300 MHz, METHANOL-d₄) δ ppm 2.39-2.51 (m, 1H) 2.55 (m, 1H) 2.80 (s, 6H) 3.07 (td, J = 8.24, 4.03 Hz, 1H) 3.18 (t, J = 8.20 Hz, 1H) 3.71 (s, 6H) 4.98 (dd, J = 8.13, 3.00 Hz, 1H) 6.74 (m, J = 8.35 Hz, 2H) 7.31 (m, J = 8.28 Hz, 2H) 7.36-7.47 (m, 2H) (hydrochloride product) | 298 |
| 11 | 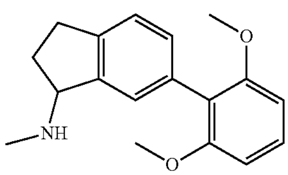 | [6-(2,6-Dimethoxy-phenyl)-indan-1-yl]-methyl-amine | 1H NMR (300 MHz, METHANOL-d₄) δ ppm 2.19-2.32 (m,, 1H) 2.64 (dt, J = 14.54, 8.11 Hz, 1H) 2.75 (s, 3H) 3.07 (dd, J = 8.79, 4.69 Hz, 1H) 3.23 (dd, J = 16.63, 7.98 Hz, 1H) 3.69 (s, 6H) 4.75 (dd, J = 7.47, 3.66 Hz, 1H) 6.73 (d, J = 8.35 Hz, 2H) 7.28 (m, 2H) 7.36 (t, J = 8.42 Hz, 1H) 7.42 (s, 1H) (hydrochloride product) | 284 |
| 12 | 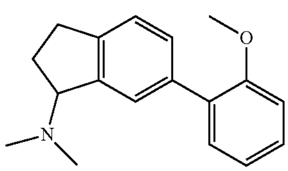 | [6-(2-Methoxy-phenyl)-indan-1-yl]-dimethyl-amine | 1H NMR (300 MHz, METHANOL-d₄) δ ppm 2.50 (m, 1H) 2.56 (m, 1H) 2.75 (s, 3H) 2.89 (s, 3H) 3.00-3.13 (m, 1H) 3.19 (t, J = 8.20 Hz, 1H) 3.81 (s, 3H) 5.04 (dd, J = 7.98, 2.86 Hz, 1H) 7.03 (m, 1H) 7.09 (d, J = 8.06 Hz, 1H) 7.28-7.39 (m, 2H) 7.44 (d, J = 7.76 Hz, 1H) 7.56 (d, J = 1.46 Hz, 1H) 7.70 (s, 1H) (hydrochloride product) | 268 |
| 13 | 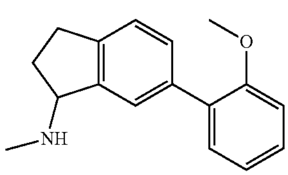 | [6-(2-Methoxy-phenyl)-indan-1-yl]-methyl-amine | 1H NMR (300 MHz, METHANOL-d₄) δ ppm 2.18-2.31 (m, 1H) 2.56-2.69 (m, 1H) 2.75 (s, 3H) 3.05 (td, J = 8.17, 4.91 Hz, 1H) 3.19 (m, 1H) 3.79 (s, 3H) 4.77 (dd, J = 7.69, 4.03 Hz, 1H) 7.01 (td, J = 7.47, 1.03 Hz, 1H) 7.08 (d, J = 7.76 Hz, 1H) 7.30 (m, 2H) 7.40 (d, J = 7.91 Hz, 1H) 7.51 (dd, J = 7.91, 1.39 Hz, 1H) 7.66 (s, 1H) (hydrochloride product) | 254 |

| Example | Structure | Name | ¹H-NMR | MS (APCI (M +H)⁺) |
|---|---|---|---|---|
| 14 | 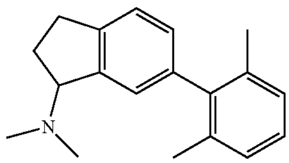 | [6-(2,6-Dimethyl-phenyl)-indan-1-yl]-dimethyl-amine | 1H NMR (300 MHz, METHANOL-d₄) δ ppm 1.89 (s, 3H) 1.93 (s, 3H) 2.32-2.56 (m, 2H) 2.60 (br. s., 3H) 2.79 (br. s., 3H) 3.03 (dd, J = 8.94, 3.37 Hz, 1H) 3.13 (d, J = 8.50 Hz, 1H) 4.96 (d, J = 5.86 Hz, 1H) 6.96-7.05 (m, 3H) 7.12 (d, J = 7.76 Hz, 1 H) 7.27 (s, 1H) 7.41 (d, J = 7.62 Hz, 1H) | 266 |
| 15 | 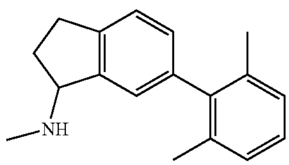 | [6-(2,6-Dimethyl-phenyl)-indan-1-yl]-methyl-amine | 1H NMR (300 MHz, METHANOL-d₄) δ ppm 1.99 (s, 3H) 2.02 (s, 3H) 2.17-2.35 (m, 1H) 2.54-2.70 (m, 1 H) 2.74 (s, 3H) 3.00-3.16 (m, 1H) 3.23 (m, 1H) 4.80 (m, 1 H) 7.02-7.14 (m, 3H) 7.18 (d, J = 7.47 Hz, 1H) 7.31 (s, 1H) 7.48 (d, J = 7.76 Hz, 1H) | 252 |
| 16 | 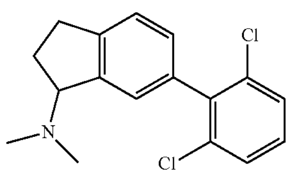 | [6-(2,6-Dichloro-phenyl)-indan-1-yl]-dimethyl-amine | | 306 |
| 17 | 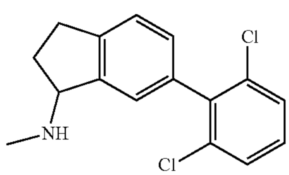 | [6-(2,6-Dichloro-phenyl)-indan-1-yl]-methyl-amine | | 292 |
| 18 | 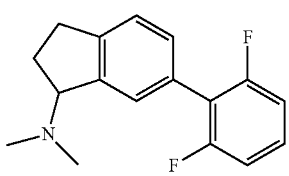 | [6-(2,6-Difluoro-phenyl)-indan-1-yl]-dimethyl-amine | | 274 |
| 19 | 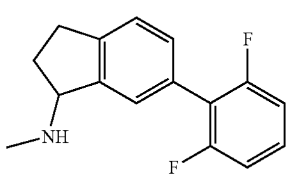 | [6-(2,6-Difluoro-phenyl)-indan-1-yl]-methyl-amine | | 259 |
| 20 | 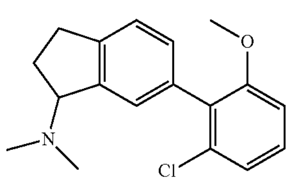 | [6-(2-Chloro-6-methoxy-phenyl)-indan-1-yl]-dimethyl-amine | 1H NMR (300 MHz, METHANOL-d₄) δ ppm 2.39-2.54 (m, 1H) 2.57-2.67 ( m, 1 H) 2.75 (s, 3H) 2.87 (s, 3H) 3.01-3.15 (m, 1H) 3.18-3.26 (m, 1H) 3.72 (s, 3H) 5.03 (dd, J = 8.06, 3.08 Hz, 1H) 7.04 (d, J = 8.50 Hz, 1H) 7.11 (d, J = 8.06 Hz, 1H) 7.26-7.39 (m, 2H) 7.45 (m, 2H) | 302 |

-continued

| Example | Structure | Name | ¹H-NMR | MS (APCI (M +H)⁺) |
|---|---|---|---|---|
| 21 | 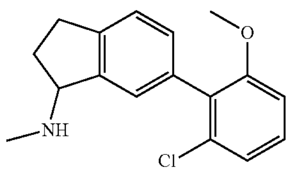 | [6-(2-Chloro-6-methoxy-phenyl)-indan-1-yl]-methyl-amine | 1H NMR (300 MHz, METHANOL-d₄) δ ppm 2.19-2.36 (m, 1H) 2.57-2.71 (m, 1 H) 2.74 (s, 3H) 3.00-3.14 (m, 1H) 3.22 (m, 1H) 3.70 (s, 3 H) 4.79 (m, 1H) 7.03 (d, J = 8.35 Hz, 1H) 7.10 (d, J = 8.06 Hz, 1H) 7.26 (d, J = 7.76 Hz, 1H) 7.33 (t, J = 8.20 Hz, 1H) 7.41 (br. s., 1H) 7.44 (d, J = 8.06 Hz, 1H) | 288 |
| 22 | 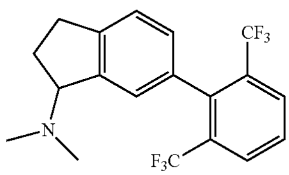 | [6-(2,6-Bis-trifluoromethyl-phenyl)-indan-1-yl]-dimethyl-amine | | 374 |
| 23 | 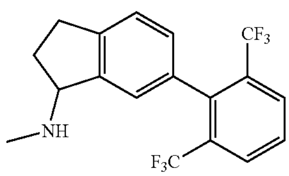 | 6-(2,6-Bis-[trifluoromethyl-phenyl)-indan-1-yl]-methyl-amine | | 360 |
| 24 | 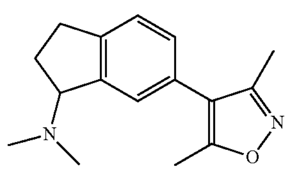 | [6-(3,5-Dimethyl-isoxazol-4-yl)-indan-1-yl]-dimethyl-amine | | 257 |
| 25 | 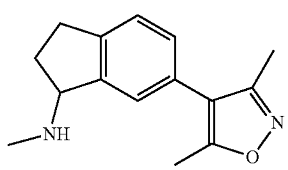 | [6-(3,5-Dimethyl-isoxazol-4-yl)-indan-1-yl]-methyl-amine | | 243 |
| 26 | 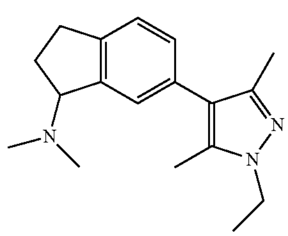 | [6-(1-Ethyl-3,5-dimethyl-1H-pyrazol-4-yl)-indan-1-yl]-dimethyl-amine | | 284 |
| 27 | 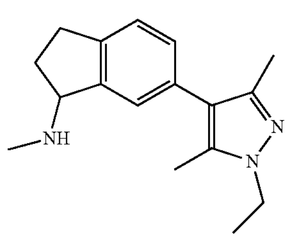 | [6-(1-Ethyl-3,5-dimethyl-1H-pyrazol-4-yl)-indan-1-yl]-methyl-amine | | 270 |

-continued

| Example | Structure | Name | ¹H-NMR | MS (APCI (M +H)⁺) |
|---|---|---|---|---|
| 28 | 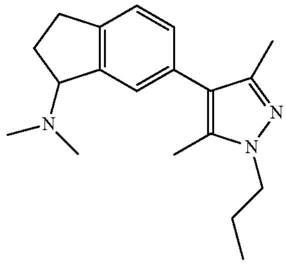 | [6-(3,5-Dimethyl-1-propyl-1H-pyrazol-4-yl)-indan-1-yl]-dimethyl-amine | | 298 |
| 29 | 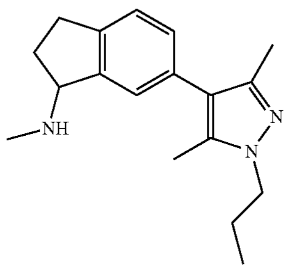 | 6-(3,5-Dimethyl-1-propyl-1H-pyrazol-4-yl)-indan-1-yl]-methyl-amine | | 284 |
| 30 | 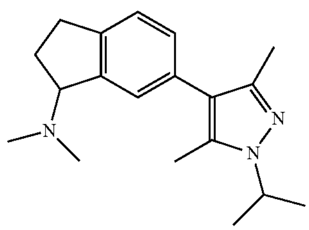 | [6-(1-Isopropyl-3,5-dimethyl-1H-pyrazol-4-yl)-indan-1-yl]-dimethyl-amine | | 297 |
| 31 | 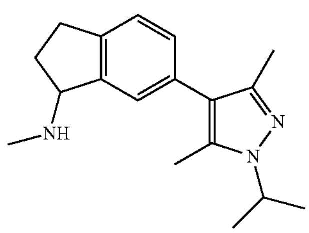 | [6-(1-Isopropyl-3,5-dimethyl-1H-pyrazol-4-yl)-indan-1-yl]-methyl-amine | | 284 |
| 32 | 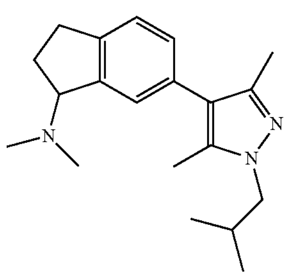 | [6-(1-Isobutyl-3,5-dimethyl-1H-pyrazol-4-yl)-indan-1-yl]-dimethyl-amine | | 312 |
| 33 | 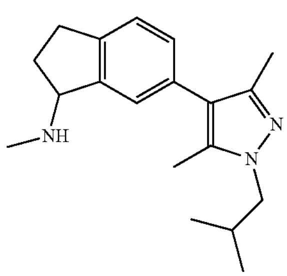 | [6-(1-Isobutyl-3,5-dimethyl-1H-pyrazol-4-yl)-indan-1-yl]-methyl-amine | | 298 |

| Example | Structure | Name | ¹H-NMR | MS (APCI (M +H)⁺) |
|---|---|---|---|---|
| 34 | 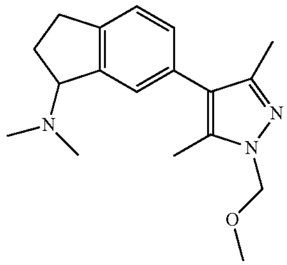 | [6-(1-Methoxymethyl-3,5-dimethyl-1H-pyrazol-4-yl)-indan-1-yl]-dimethyl-amine | | 300 |
| 35 | 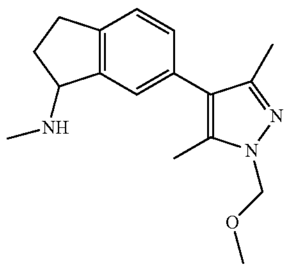 | [6-(1-Methoxymethyl-3,5-dimethyl-1H-pyrazol-4-yl)-indan-1-yl]-methyl-amine | | 286 |
| 36 | 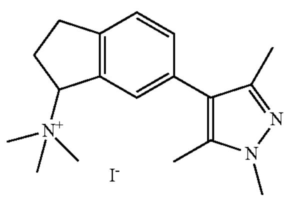 | Trimethyl-[6-(1,3,5-trimethyl-1H-pyrazol-4-yl)-indan-1-yl]-ammonium iodide | 1H NMR (300 MHz, METHANOL-d₄) δ ppm 2.19 (s, 3H) 2.26 (s, 3H) 2.50-2.67 (m, 1H) 2.73-2.81 (m, 1 H) 2.99-3.18 (m, 1H) 3.13 (s, 9H) 3.24 (m, 1H) 3.77 (s, 3 H) 5.04 (d, J = 7.91 Hz, 1H) 7.40 (m, 1H) 7.52 (m, 2H) | 284 |
| 37 | 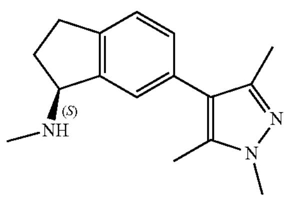 | (S) Methyl-[6-(1,3,5-trimethyl-1H-pyrazol-4-yl)-indan-1-yl]-amine | 1H NMR (400 MHz, METHANOL-d₄) □ ppm 2.24-2.37 (m, 1H) 2.40 (s, 6H) 2.56-2.71 (m, 1H) 2.77 (s, 3 H) 3.02-3.12 (m, 1H) 3.24 (m, J = 8.16 Hz, 1H) 4.02 (s, 3 H) 4.85 (m, 1H) 7.39 (d, J = 6.87 Hz, 1H) 7.53 (d, J = 7.73 Hz, 1H) 7.67 (s, 1H) (dihydrochloride product) | 256 |
| 38 | 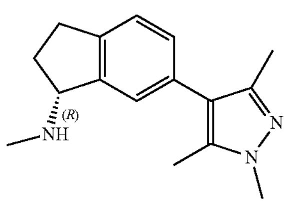 | (R) Methyl-[6-(1,3,5-trimethyl-1H-pyrazol-4-yl)-indan-1-yl]-amine | 1H NMR (400 MHz, METHANOL-d₄) □ ppm 2.24-2.37 (m, 1H) 2.40 (s, 6H) 2.56-2.71 (m, 1H) 2.77 (s, 3 H) 3.02-3.12 (m, 1H) 3.24 (m, J = 8.16 Hz, 1H) 4.02 (s, 3 H) 4.85 (m, 1H) 7.39 (d, J = 6.87 Hz, 1H) 7.53 (d, J = 7.73 Hz, 1H) 7.67 (s, 1H) (dihydrochloride product) | 256 |
| 39 | 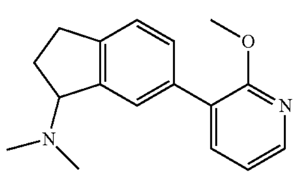 | [6-(2-Methoxy-pyridin-3-yl)-indan-1-yl]-dimethyl-amine | | 269 |
| 40 | 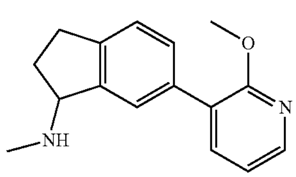 | [6-(2-Methoxy-pyridin-3-yl)-indan-1-yl]-methyl-amine | | 255 |

| Example | Structure | Name | ¹H-NMR | MS (APCI (M+H)⁺) |
|---|---|---|---|---|
| 41 | 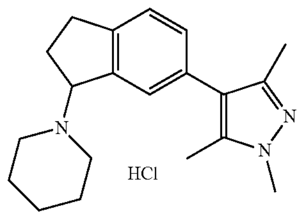 | Dimethyl-(6-piperidin-1-yl-indan-1-yl)-amine; hydrochloride | | 310 |
| 42 | 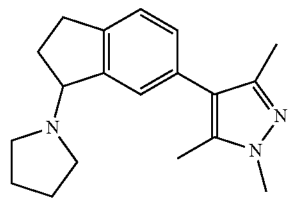 | Dimethyl-(6-pyrrolidin-1-yl-indan-1-yl)-amine | | 296 |

Pharmacological Data:

Results for representative compounds/examples are given in the table below:

| COMPOUND/ EXAMPLE | 5-HT₇ IC₅₀ (nM) | 5-HT₇ K$_i$ (nM) |
|---|---|---|
| 1 | 15.5 ± 2.9 | |
| 2 | 5.5 ± 2.7 | |
| 3 | 307 ± 181 | |
| 4 | 18.7 | |
| 10 | 53.5 ± 10.1 | |
| 11 | 195 ± 86 | |
| 12 | 68.4 ± 1.1 | |
| 13 | 77.7 ± 40.9 | |
| 14 | | 197.7 ± 31.9 |
| 15 | | 75.2 ± 2 |
| 19 | | 47.6 ± 1.2 |
| 20 | | 25.8 ± 2.7 |
| 21 | | 55.7 ± 1.2 |
| 36 | | 152.9 ± 32.4 |
| 38 | | 73.3 ± 9.3 |

Formulation Example

Example of a Tablet Formulation

| | |
|---|---|
| Compound according to example 1 | 5 mg |
| Lactose | 60 mg |
| Crystalline cellulose | 25 mg |
| Povidone K 90 | 5 mg |
| Pregelanitized starch | 3 mg |
| Colloidal silica dioxide | 1 mg |
| Magnesium stearate | 1 mg |
| Total weight per tablet | 100 mg |

The above mentioned ingredients were mixed and compressed into a tablet by conventional methods known to those skilled in the art.

X-Ray-Analysis of the Crystal Structure of Example 1

The crystal structure of Example 1 was analysed under X-Ray and is shown in FIGS. 1 and 2.

Experimental

Crystal structure determination was carried out using a Bruker-Nonius diffractometer equipped with a APPEX 2 4K CCD area detector, a FR591 rotating anode with Mo$_{K\alpha}$ radiation, Montel mirrors as monochromator and a Kryoflex low temperature device (T=100 K). Fullsphere data collection omega and phi scans. Programs used: Data collection Apex2 V. 1.0-22 (Bruker-Nonius 2004), data reduction Saint+Version 6.22 (Bruker-Nonius 2001) and absorption correction SADABS V. 2.10 (2003). Crystal structure solution was achieved using direct methods as implemented in SHELXTL Version 6.10 (Sheldrick, Universtitat GOttingen (Germany), 2000) and visualized using XP program. Missing atoms were subsequently located from difference Fourier synthesis and added to the atom list. Least-squares refinement on F2 using all measured intensities was carried out using the program SHELXTL Version 6.10 (Sheldrick, Universtitat GOttingen (Germany), 2000). All non hydrogen atoms were refined including anisotropic displacement parameters.

Tables

TABLE 1

Crystal data and structure refinement for p01215_0m.

| | |
|---|---|
| Identification code | p01215_0m |
| Empirical formula | C34H50Cl4N6 |
| Formula weight | 684.60 |
| Temperature | 100(2) K |
| Wavelength | 0.71073 Å |

TABLE 1-continued

Crystal data and structure refinement for p01215__0m.

| | | |
|---|---|---|
| Crystal system | Monoclinic | |
| Space group | $P2_1$ | |
| Unit cell dimensions | a = 6.0395(2) Å | a = 90°. |
| | b = 15.0539(4) Å | b = 102.534(2)°. |
| | c = 10.5764(3) Å | g = 90°. |
| Volume | 938.67(5) Å$^3$ | |
| Z | 1 | |
| Density (calculated) | 1.211 Mg/m$^3$ | |
| Absorption coefficient | 0.346 mm$^{-1}$ | |
| F(000) | 364 | |
| Crystal size | 0.10 × 0.10 × 0.10 mm$^3$ | |
| Theta range for data collection | 3.35 to 36.38°. | |
| Index ranges | $-9 \leq h \leq 4, -23 \leq k \leq 25, -14 \leq l \leq 14$ | |
| Reflections collected | 7260 | |
| Independent reflections | 4838 [R(int) = 0.0323] | |
| Completeness to theta = 36.38° | 83.9% | |
| Absorption correction | None | |
| Max. and min. transmission | 0.9662 and 0.9662 | |
| Refinement method | Full-matrix least-squares on F$^2$ | |
| Data/restraints/parameters | 4838/1/204 | |
| Goodness-of-fit on F$^2$ | 1.053 | |
| Final R indices [I > 2sigma(I)] | R1 = 0.0386, wR2 = 0.0958 | |
| R indices (all data) | R1 = 0.0420, wR2 = 0.0992 | |
| Absolute structure parameter | −0.04(4) | |
| Largest diff. peak and hole | 0.688 and −0.341 e · Å$^{-3}$ | |

TABLE 2

Bond lengths [Å] and angles [°] for p01215__0m.

| | | | |
|---|---|---|---|
| N(1)—C(2) | 1.341(2) | N(3)—C(10) | 1.5147(18) |
| N(1)—N(2) | 1.3492(16) | C(7)—C(8) | 1.398(2) |
| N(1)—C(5) | 1.455(2) | C(7)—C(15) | 1.4049(19) |
| C(1)—C(3) | 1.3989(19) | C(8)—C(9) | 1.389(2) |
| C(1)—C(2) | 1.4014(19) | C(9)—C(13) | 1.3977(18) |
| C(1)—C(7) | 1.474(2) | C(9)—C(10) | 1.508(2) |
| N(2)—C(3) | 1.333(2) | C(10)—C(11) | 1.546(2) |
| C(2)—C(4) | 1.4837(18) | C(11)—C(12) | 1.547(2) |
| C(3)—C(6) | 1.4895(19) | C(12)—C(13) | 1.501(2) |
| N(3)—C(16) | 1.4877(19) | C(13)—C(14) | 1.393(2) |
| N(3)—C(17) | 1.490(2) | C(14)—C(15) | 1.392(2) |
| C(2)—N(1)—N(2) | 109.27(12) | C(8)—C(7)—C(1) | 120.71(11) |
| C(2)—N(1)—C(5) | 130.14(12) | C(15)—C(7)—C(1) | 120.46(13) |
| N(2)—N(1)—C(5) | 120.37(14) | C(9)—C(8)—C(7) | 119.43(12) |
| C(3)—C(1)—C(2) | 105.90(13) | C(8)—C(9)—C(13) | 121.46(13) |
| C(3)—C(1)—C(7) | 126.84(12) | C(8)—C(9)—C(10) | 128.00(12) |
| C(2)—C(1)—C(7) | 127.26(12) | C(13)—C(9)—C(10) | 110.53(13) |
| C(3)—N(2)—N(1) | 109.40(12) | C(9)—C(10)—N(3) | 111.16(12) |
| N(1)—C(2)—C(1) | 107.51(11) | C(9)—C(10)—C(11) | 103.93(11) |
| N(1)—C(2)—C(4) | 121.35(13) | N(3)—C(10)—C(11) | 113.86(12) |
| C(1)—C(2)—C(4) | 131.11(14) | C(10)—C(11)—C(12) | 106.47(13) |
| N(2)—C(3)—C(1) | 107.90(12) | C(13)—C(12)—C(11) | 103.43(12) |
| N(2)—C(3)—C(6) | 120.17(14) | C(14)—C(13)—C(9) | 119.58(14) |
| C(1)—C(3)—C(6) | 131.84(15) | C(14)—C(13)—C(12) | 128.90(13) |
| C(16)—N(3)—C(17) | 111.11(12) | C(9)—C(13)—C(12) | 111.52(13) |
| C(16)—N(3)—C(10) | 113.89(11) | C(15)—C(14)—C(13) | 119.03(12) |
| C(17)—N(3)—C(10) | 111.82(13) | C(14)—C(15)—C(7) | 121.68(13) |
| C(8)—C(7)—C(15) | 118.83(13) | | |

TABLE 3

Torsion angles [°] for p01215__0m.

| | | | |
|---|---|---|---|
| C(2)—N(1)—N(2)—C(3) | −1.29(18) | C(7)—C(8)—C(9)—C(10) | −177.70(13) |
| C(5)—N(1)—N(2)—C(3) | −176.32(15) | C(8)—C(9)—C(10)—N(3) | −69.32(18) |
| N(2)—N(1)—C(2)—C(1) | 1.44(17) | C(13)—C(9)—C(10)—N(3) | 112.00(13) |
| C(5)—N(1)—C(2)—C(1) | 175.84(17) | C(8)—C(9)—C(10)—C(11) | 167.80(14) |
| N(2)—N(1)—C(2)—C(4) | −176.87(14) | C(13)—C(9)—C(10)—C(11) | −10.88(15) |
| C(5)—N(1)—C(2)—C(4) | −2.5(3) | C(16)—N(3)—C(10)—C(9) | −60.72(16) |
| C(3)—C(1)—C(2)—N(1) | −1.06(17) | C(17)—N(3)—C(10)—C(9) | 172.29(11) |
| C(7)—C(1)—C(2)—N(1) | 178.62(14) | C(16)—N(3)—C(10)—C(11) | 56.24(18) |
| C(3)—C(1)—C(2)—C(4) | 177.03(15) | C(17)—N(3)—C(10)—C(11) | −70.75(15) |
| C(7)—C(1)—C(2)—C(4) | −3.3(3) | C(9)—C(10)—C(11)—C(12) | 18.96(15) |

TABLE 3-continued

| Torsion angles [°] for p01215_0m. | | | |
|---|---|---|---|
| N(1)—N(2)—C(3)—C(1) | 0.59(19) | N(3)—C(10)—C(11)—C(12) | −102.12(14) |
| N(1)—N(2)—C(3)—C(6) | 177.48(14) | C(10)—C(11)—C(12)—C(13) | −19.90(15) |
| C(2)—C(1)—C(3)—N(2) | 0.29(18) | C(8)—C(9)—C(13)—C(14) | −0.3(2) |
| C(7)—C(1)—C(3)—N(2) | −179.38(13) | C(10)—C(9)—C(13)—C(14) | 178.45(13) |
| C(2)—C(1)—C(3)—C(6) | −176.11(17) | C(8)—C(9)—C(13)—C(12) | 179.33(14) |
| C(7)—C(1)—C(3)—C(6) | 4.2(3) | C(10)—C(9)—C(13)—C(12) | −1.89(17) |
| C(3)—C(1)—C(7)—C(8) | 47.3(2) | C(11)—C(12)—C(13)—C(14) | −166.61(15) |
| C(2)—C(1)—C(7)—C(8) | −132.35(15) | C(11)—C(12)—C(13)—C(9) | 13.78(16) |
| C(3)—C(1)—C(7)—C(15) | −133.25(16) | C(9)—C(13)—C(14)—C(15) | −0.4(2) |
| C(2)—C(1)—C(7)—C(15) | 47.1(2) | C(12)—C(13)—C(14)—C(15) | −179.97(15) |
| C(15)—C(7)—C(8)—C(9) | −0.7(2) | C(13)—C(14)—C(15)—C(7) | 0.6(2) |
| C(1)—C(7)—C(8)—C(9) | 178.84(13) | C(8)—C(7)—C(15)—C(14) | 0.0(2) |
| C(7)—C(8)—C(9)—C(13) | 0.9(2) | C(1)—C(7)—C(15)—C(14) | −179.54(14) |

The invention claimed is:

1. A compound, or a salt thereof, of general formula (I)

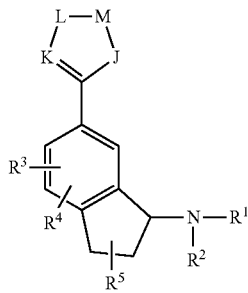

(I)

wherein

K-L-M-J together form

=CH—X—Y=CH—; in which any suitable H may be substituted by $R^6$ or $R^7$, and in which X is selected from $NR^8$, O and S, while Y is selected from N and CH;

=CH—X—Y—C(O)—; in which any suitable H may be substituted by $R^6$ and in which one of X and Y is $NR^8$, while the other is selected from $NR^{8a}$, S and O;

=CH—X—Y—C(O)—; in which one of X and Y is $CH_2$, while the other is selected from $NR^8$, S and O, in which any suitable H may be substituted by $R^6$ or $R^7$;

=$CR^6$—N=N—C(O)—;

=$CR^9$—CH=CH—CH=CH—; in which any suitable H may be substituted by $R^6$;

=$CR^9$—CH=CH—CH=$CR^{9a}$—; in which any suitable H may be substituted by $R^6$;

=CH—X=Y—CH=CH—; in which any suitable H may be substituted by $R^6$ or $R^7$, and in which one of X or Y is selected from N, while the other is selected from N and CH;

=CH—X=Y—$CH_2$—$CH_2$—; in which any suitable H may be substituted by $R^6$ or $R^7$, and in which one of X or Y is selected from N, while the other is selected from N and CH;

=CH—X—Y—CH=CH—; in which any suitable H may be substituted by $R^6$ or $R^7$, and in which one of X or Y is selected from $NR^8$, O and S while the other is selected from $NR^{8a}$ and $CH_2$;

=CH—X—Y—$CH_2$—$CH_2$—; in which any suitable H may be substituted by $R^6$ or $R^7$, and in which one of X or Y is selected from $NR^8$, O and S while the other is selected from $NR^{8a}$ and $CH_2$;

=CH—X—$CH_2$—Y=CH—; in which any suitable H may be substituted by $R^6$ or $R^7$, and in which X is selected from $NR^8$, O and S while Y is selected from N and CH;

=CH—X—CH=Y—$CH_2$—; in which any suitable H may be substituted by $R^6$ or $R^7$, and in which X is selected from $NR^8$, O and S while Y is selected from N and CH;

=CH—N=CH—Y=CH—; in which any suitable H may be substituted by $R^6$ or $R^7$, and in which Y is CH;

=CH—X—$CH_2$—Y—$CH_2$—; in which any suitable H may be substituted by $R^6$ or $R^7$, and in which one of X or Y is selected from $NR^8$, O and S while the other is selected from $NR^{8a}$, O, S and $CH_2$;

$R^1$ and $R^2$ each are independently selected from the group consisting of hydrogen; and a linear or branched, saturated or unsaturated, optionally at least mono-substituted aliphatic radical;

or $R^1$ and $R^2$ together with the bridging nitrogen atom form a saturated or unsaturated, optionally at least mono-substituted 5-or 6 membered-heterocyclic ring, which may be condensed with an optionally at least mono-substituted mono-or polycyclic ringsystem;

$R^3$, $R^4$ and $R^5$ are independently from each other selected from hydrogen; halogen, OH, SH, $NH_2$; a linear or branched, saturated or unsaturated, optionally at least mono-substituted aliphatic radical; and O-R with R being a linear or branched, saturated or unsaturated, optionally at least mono-substituted aliphatic radical;

$R^6$ and $R^7$ are independently from each other selected from hydrogen; halogen, OH, SH, $NH_2$; an aliphatic radical, which is linear or branched, saturated or unsaturated, and optionally at least mono-substituted by F, Cl, Br, I, SH or OH; and O—R with R being an aliphatic radical, which is linear or branched, saturated or unsaturated, and optionally at least mono-substituted by F, Cl, Br, I, SH or OH;

$R^8$ and $R^{8a}$ are independently from each other selected from hydrogen; halogen, OH, SH, $NH_2$; an aliphatic radical, which is linear or branched, saturated or unsaturated, and optionally at least mono-substituted by F, Cl, Br, I, SH or OH; and —R'—O—R" with R' and R" independently from one another being a $C_{1-6}$-alkyl radical, which is linear or branched, and optionally at least mono-substituted by F, Cl, Br, I, SH or OH;

$R^9$ and $R^{9a}$ are independently from each other selected from halogen; an aliphatic radical, which is linear or branched, saturated or unsaturated, and optionally at least mono-substituted by F, Cl, Br, I, SH or OH; and O—R with R being an aliphatic radical, which is linear or branched, saturated or unsaturated, and optionally at least mono-substituted by F, Cl, Br, I, SH or OH;

in which $NR^1R^2$ of general formula (I) is substituted by an additional methyl to form with $R^1$ and $R^2$ being $CH_3$ a trimethyl-ammonium-radical.

2. The compound or salt according to claim 1, of Formula Ia

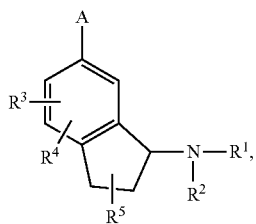

(Ia)

wherein
A is a compound selected from the following group

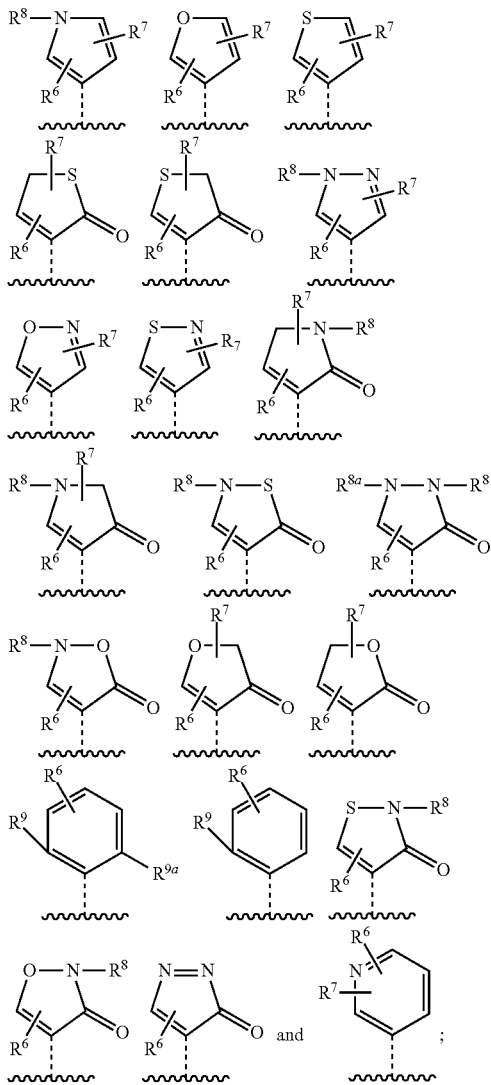

$R^1$ and $R^2$ each are independently selected from the group consisting of hydrogen; and a linear or branched, saturated or unsaturated, optionally at least mono-substituted aliphatic radical; or $R^1$ and $R^2$ together with the bridging nitrogen atom form an saturated or unsaturated, optionally at least mono-substituted 5- or 6-membered-heterocyclic ring, which may be condensed with an optionally at least mono-substituted mono- or polycyclic ringsystem;

$R^3$, $R^4$ and $R^5$ are independently from each other selected from hydrogen; halogen, OH, SH, $NH_2$; a linear or branched, saturated or unsaturated, optionally at least mono-substituted aliphatic radical; and O—R with R being a linear or branched, saturated or unsaturated, optionally at least mono-substituted aliphatic radical;

$R^6$ and $R^7$ are independently from each other selected from hydrogen; halogen, OH, SH, $NH_2$; an aliphatic radical, which is linear or branched, saturated or unsaturated, and optionally at least mono-substituted by F, Cl, Br, I, SH or OH; and O—R with R being an aliphatic radical, which is linear or branched, saturated or unsaturated, and optionally at least mono-substituted by F, Cl, Br, I, SH or OH;

$R^9$ and $R^{8a}$ are independently from each other selected from hydrogen; an aliphatic radical, which is linear or branched, saturated or unsaturated, and optionally at least mono-substituted by F, Cl, Br, I, SH or OH; and —R'—O—R" with R' and R" independently from one another being a $C_{1-6}$-alkyl radical, which is linear or branched, and optionally at least mono-substituted by F, Cl, Br, I, SH or OH;

$R^9$ and $R^{9a}$ are independently from each other selected from halogen; an aliphatic radical, which is linear or branched, saturated or unsaturated, and optionally at least mono-substituted by F, Cl, Br, I, SH or OH; and O—R with R being an aliphatic radical, which is linear or branched, saturated or unsaturated, and optionally at least mono-substituted by F, Cl, Br, I, SH or OH.

3. The compound or salt according to claim 2, wherein

A is a compound selected from the following group

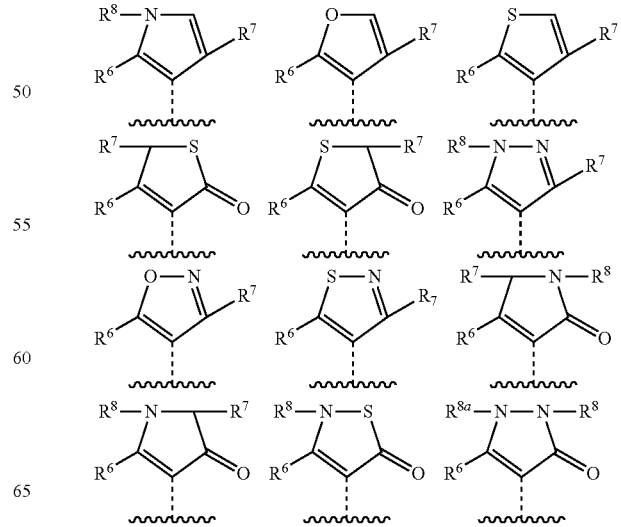

-continued

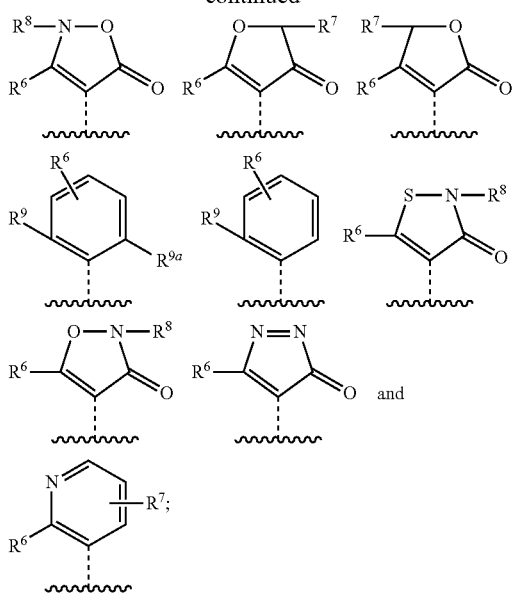

R¹ and R² each are independently selected from the group consisting of hydrogen; and a linear or branched, saturated or unsaturated, optionally at least mono-substituted aliphatic radical; or R¹ and R² together with the bridging nitrogen atom form saturated or unsaturated, optionally at least mono-substituted 5- or 6-membered-heterocyclic ring, which may be condensed with an optionally at least mono-substituted mono- or polycyclic ringsystem, R³, R⁴ and R⁵ are independently from each other selected from hydrogen; halogen, OH, SH, NH₂; a linear or branched, saturated or unsaturated, optionally at least mono-substituted aliphatic radical; and O—R with R being a linear or branched, saturated or unsaturated, optionally at least mono-substituted aliphatic radical;

R⁶ and R⁷ are independently from each other selected from hydrogen; halogen, OH, SH, NH₂; an aliphatic radical, which is linear or branched, saturated or unsaturated, and optionally at least mono-substituted by F, Cl, Br, I, SH or OH; and O—R with R being an aliphatic radical, which is linear or branched, saturated or unsaturated, and optionally at least mono-substituted by F, Cl, Br, I, SH or OH;

R⁸ and R⁸ᵃ are independently from each other selected from hydrogen; an aliphatic radical, which is linear or branched, saturated or unsaturated, and optionally at least mono-substituted by F, Cl, Br, I, SH or OH; and —R'—O—R" with R' and R" independently from one another being a C₁₋₆-alkyl radical, which is linear or branched, and optionally at least mono-substituted by F, Cl, Br, I, SH or OH;

R⁹ and R⁹ᵃ are independently from each other selected from halogen; an aliphatic radical, which is linear or branched, saturated or unsaturated, and optionally at least mono-substituted by F, Cl, Br, I, SH or OH; and O—R with R being an aliphatic radical, which is linear or branched, saturated or unsaturated, and optionally at least mono-substituted by F, Cl, Br, I, SH or OH.

4. The Compound or salt according to claim 2, wherein A is a compound selected from the following group

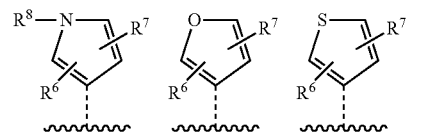

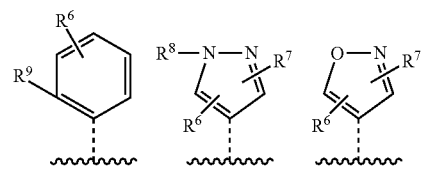

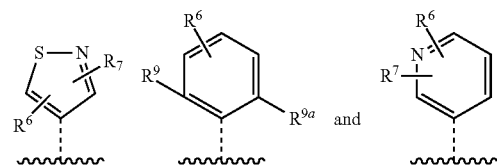

R¹ and R² each are independently selected from the group consisting of hydrogen; and a linear or branched, saturated or unsaturated, optionally at least mono-substituted aliphatic radical; or R¹ and R² together with the bridging nitrogen atom form an saturated or unsaturated, optionally at least mono-substituted 5- or 6-membered-heterocyclic ring, which may be condensed with an optionally at least mono-substituted mono- or polycyclic ringsystem;

R³, R⁴ and R⁵ are independently from each other selected from hydrogen; halogen, OH, SH, NH₂; a linear or branched, saturated or unsaturated, optionally at least mono-substituted aliphatic radical; and O—R with R being a linear or branched, saturated or unsaturated, optionally at least mono-substituted aliphatic radical;

R⁶ and R⁷ are independently from each other selected from hydrogen; halogen, OH, SH, NH₂; an aliphatic radical, which is linear or branched, saturated or unsaturated, and optionally at least mono-substituted by F, Cl, Br, I, SH or OH; and O—R with R being an aliphatic radical, which is linear or branched, saturated or unsaturated, and optionally at least mono-substituted by F, Cl, Br, I, SH or OH;

R⁸ is selected from hydrogen; an aliphatic radical, which is linear or branched, saturated or unsaturated, and optionally at least mono-substituted by F, Cl, Br, I, SH or OH; and —R'—O—R" with R' and R" independently from one another being a C₁₋₆-alkyl radical, which is linear or branched, and optionally at least mono-substituted by F, Cl, Br, I, SH or OH R⁹ and R⁹ᵃ are independently from each other selected from halogen; an aliphatic radical, which is linear or branched, saturated or unsaturated, and optionally at least mono-substituted by F, Cl, Br, I, SH or OH; and O—R with R being an aliphatic radical, which is linear or branched, saturated or unsaturated, and optionally at least mono-substituted by F, Cl, Br, I, SH or OH.

5. The compound or salt according to claim 4, wherein A is a compound selected from the following group

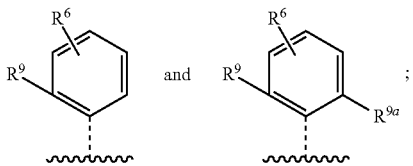

R¹ and R² each are independently selected from the group consisting of hydrogen; and a linear or branched, saturated or unsaturated, optionally at least mono-substituted aliphatic radical; or R¹ and R² together with the bridging nitrogen atom form an saturated or unsaturated, optionally at least mono-substituted 5- or 6-membered-heterocyclic ring, which may be condensed with an optionally at least mono-substituted mono- or polycyclic ringsystem;

R³, R⁴ and R⁵ are independently from each other selected from hydrogen; halogen, OH, SH, NH₂; a linear or branched, saturated or unsaturated, optionally at least mono-substituted aliphatic radical; and O—R with R being a linear or branched, saturated or unsaturated, optionally at least mono-substituted aliphatic radical;

R⁶ is selected from hydrogen; halogen, OH, SH, NH₂; an aliphatic radical, which is linear or branched, saturated or unsaturated, and optionally at least mono-substituted by F, Cl, Br, I, SH or OH; and O—R with R being an aliphatic radical, which is linear or branched, saturated or unsaturated, and optionally at least mono-substituted by F, Cl, Br, I, SH or OH;

R⁹ and R⁹ᵃ are independently from each other selected from halogen; an aliphatic radical, which is liner or branched, saturated or unsaturated, and optionally at least mono-substituted by F, CL, Br, I, SH or OH; and O—R with R being an aliphatic radical, which is linear or branched, saturated or unsaturated, and optionally at least mono-substituted by F, Cl, Br, I, SH or OH.

6. The Compound or salt according to claim 1, wherein R¹ and R² each are independently selected from the group consisting of hydrogen; and a linear or branched, optionally at least mono-substituted C₁₋₄-alkyl radical; or R¹ and R² together with the bridging nitrogen atom form an saturated or unsaturated, optionally at least mono-substituted 5- or 6-membered-heterocyclic ring.

7. The Compound or salt according to claim 1, wherein R³, R⁴ and R⁵ are independently from each other selected from H, F, Cl, Br, I, OH, SH, NH₂, CH₃, C₂H₅, C₃H₇, C₄H₉, OCH₃, OC₂H₅, OC₃H₇ and OC₄H₉.

8. The compound or salt according to claim 1, wherein R⁶ and R⁷ are independently from each other selected from H, F, Cl, Br, I, OH, SH, NH₂, CH₃, C₂H₅, C₃H₇, C₄H₉, OCH₃, OC₂H₅, OC₃H₇ and OC₄H₉.

9. The Compound or salt according to, claim 1, wherein R⁸ is selected from hydrogen; halogen, OH, SH, NH₂; a C₁₋₄-alkyl radical, which is linear or branched, and optionally at least mono-substituted by F, Cl, Br, I, SH or OH; and —(CH₂)ₚ—O—(CH₂)_q with p and q independently from one another being 1, 2, 3 or 4.

10. Compound or salt according to claim 1, selected from
Dimethyl-[6-(1,3,5-trimethyl-1H-pyrazol-4-yl)-indan-1-yl]-amine;
(R) Dimethyl-[6-(1,3,5-trimethyl-1H-pyrazol-4-yl)-indan-1-l]-amine;
(S) Dimethyl-[6-(1,3,5-trimethyl-1H-pyrazol-4-yl)-indan-1-l]-amine;
Methyl-[6-(1,3,5-trimethyl-1H-pyrazol-4-yl)-indan-1-yl]-amine;
6-(1,3,5-Trimethyl-1H-pyrazol-4-yl)-indan-1-ylamine;
Diethyl-[6-(1,3,5-trimethyl-1H-pyrazol-4-yl)-indan-1-yl]-amine;
Dipropyl-[6-(1,3,5-trimethyl-1H-pyrazol-4-yl)-indan-1-yl]-amine;
[6-(3,5-Dimethyl-1H-pyrazol-4-yl)-indan-1-yl]-dimethyl-amine;
[6-(3,5-Dimethyl-1H-pyrazol-4-yl)-indan-1-yl]-methyl-amine;
[6-(3,5-Dimethyl-isoxazol-4-yl)-indan-1-yl]-dimethyl-amine;
[6-(3,5-Dimethyl-isoxazol-4-yl)-indan-1-yl]-methyl-amine;
[6-(1-Ethyl-3,5-dimethyl-1H-pyrazol-4-yl)-indan-1-yl]-dimethyl-amine;
[6-(1-Ethyl-3,5-dimethyl-1H-pyrazol-4-yl)-indan-1-yl]-methyl-amine;
[6-(3,5-Dimethyl-1-propyl-1H-pyrazol-4-yl)-indan-1-yl]-dimethyl-amine;
[6-(3,5-Dimethyl-1-propyl-1H-pyrazol-4-yl)-indan-1-yl]-methyl-amine;
[6-(1-Isopropyl-3,5-dimethyl-1H-pyrazol-4-yl)-indan-1-yl]-dimethyl-amine;
[6-(1-Isopropyl-3,5-dimethyl-1H-pyrazol-4-yl)-indan-1-yl]-methyl-amine;
[6-(1-Isobutyl-3,5-dimethyl-1H-pyrazol-4-yl)-indan-1-yl]-dimethyl-amine;
[6-(1-Isobutyl-3,5-dimethyl-1H-pyrazol-4-yl)-indan-1-yl]-methyl-amine;
[6-(1-Methoxymethyl-3,5-dimethyl-1H-pyrazol-4-yl)-indan-1-yl]-dimethyl-amine;
[6-(1-Methoxymethyl-3,5-dimethyl-1H-pyrazol-4-yl)-indan-1-yl]-methyl-amine;
Trimethyl-[6-(1,3,5-trimethyl-1H-pyrazol-4-yl)-indan-1-yl]-ammonium iodide;
(S) Methyl-[6-(1,3,5-trimethyl-1H-pyrazol-4-yl)-indan-1-yl]-amine;
(R) Methyl-[6-(1,3,5-trimethyl-1H-pyrazol-4-yl)-indan-1-yl]-amine;
[6-(2-Methoxy-pyridin-3-yl)-indan-1-yl]-dimethyl-amine;
[6-(2-Methoxy-pyridin-3-yl)-indan-1-yl]-methyl-amine;
Dimethyl-(6-piperidin-1-yl-indan-1-yl)-amine; hydrochloride; and
Dimethyl-(6-pyrrolidin-1-yl-indan-1-yl)-amine;
in which NR¹R² of general formula (I) is optionally substituted by an additional methyl to form with R¹ and R² being CH₃ a trimethyl-ammonium-radical.

11. Compound or salt according to claim 1, wherein R⁹ and R⁹ᵃ are independently from each other selected from F, Cl, Br, I, CH₃, CF₃, C₂H₅, C₃H₇, C₄H₉, OCH₃, OC₂H₅, OC₃H₇ and OC₄H₉.

12. The Compound or salt according to claim 1, selected from
[6-(2,6-Dimethoxy-phenyl)-indan-1-yl]-dimethyl-amine;
[6-(2,6-Dimethoxy-phenyl)-indan-1-yl]-methyl-amine;
[6-(2-Methoxy-phenyl)-indan-1-yl]-dimethyl-amine;
[6-(2-Methoxy-phenyl)-indan-1-yl]-methyl-amine;
[6-(2,6-Dimethyl-phenyl)-indan-1-yl]-dimethyl-amine;
[6-(2,6-Dimethyl-phenyl)-indan-1-yl]-methyl-amine;
[6-(2,6-Dichloro-phenyl)-indan-1-yl]-dimethyl-amine;
[6-(2,6-Dichloro-phenyl)-indan-1-yl]-methyl-amine;
[6-(2,6-Difluoro-phenyl)-indan-1-yl]-dimethyl-amine;

[6-(2,6-Difluoro-phenyl)-indan-1-yl]-methyl-amine;
[6-(2-Chloro-6-methoxy-phenyl)-indan-1-yl]-dimethyl-amine;
[6-(2-Chloro-6-methoxy-phenyl)-indan-1-yl]-methyl-amine;
[6-(2,6-Bis-trifluoromethyl-phenyl)-indan-1-yl]-dimethyl-amine; and
[6-(2,6-Bis-trifluoromethyl-phenyl)-indan-1-yl]-methyl-amine;

in which $NR^1R^2$ of general formula (I) is optionally substituted by an additional methyl to form with $R^1$ and $R^2$ being $CH_3$ a trimethyl-ammonium-radical.

13. A process for the preparation of compounds or salts thereof according to claim 1, characterized in that a compound of general formula (III)

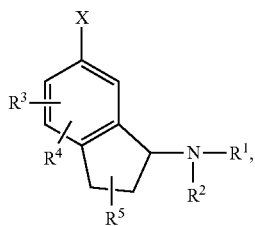

wherein $R^1, R^2, R^3, R^4$ and $R^5$ are as defined in claim 1, and X represents halogen, OH, $OCH_3$ or an O-triflate group, is reacted with a compound of general formula IIb or IIc

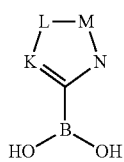
(IIb)

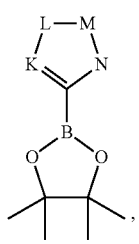
(IIc)

wherein K, L, M, and N are as defined in claim 1, to form a compound according to formula I.

14. The process according to claim 13, wherein at least one of the following conditions is met:
a) the catalyst is a palladium catalyst;
b) a ligand is present;
c) the reaction is carried out in presence of at least one base, selected from organic or inorganic bases;
d) the reaction is carried out in a suitable reaction medium.

15. A composition comprising at least one compound or salt thereof according to claim 1 and optionally one or more pharmaceutically acceptable adjuvants.

16. A method for the treatment of a 5-$HT_7$ mediated disease or condition, which method comprises administering to a subject in need a therapeutically effective amount of at least one compound, or salt thereof, according to claim 1, and optionally one or more pharmaceutically acceptable adjuvants, wherein said disease or condition is pain.

17. The compound or salt according to claim 4 wherein A is a compound selected from the following group

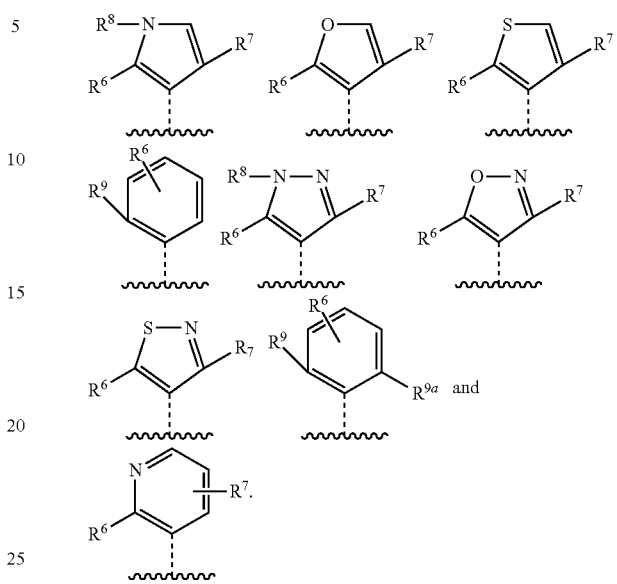

18. The compound or salt according to claim 6 wherein $R^1$ and $R^2$ are each independently selected from the group consisting of hydrogen, $CH_3$, $C_2H_5$ and $C_3H_7$.

19. The compound or salt according to claim 7 wherein $R^3$, $R^4$ and $R^5$ are each H.

20. The compound or salt according to claim 8 wherein $R^6$ and $R^7$ are independently from each other selected from H or $CH_3$.

21. Compound or salt according to claim 9 wherein $R^8$ is selected from H, F, Cl, Br, I, OH, SH, $NH_2$, $CH_3$, $C_2H_5$, $C_3H_7$, $C_4H_9$, $CH_2$—O—$CH_3$ and $CH_2$—O—$C_2H_5$.

22. The Compound or salt according to claim 21 wherein $R^8$ is selected from H, $CH_3$, $C_2H_5$, $C_3H_7$, $C_4H_9$, and $CH_2$—O—$CH_3$.

23. The Compound or salt according to claim 11 wherein $R^9$ and $R^{9a}$ are independently from each other selected from F, Cl, $CH_3$, $CF_3$ and $OCH_3$.

24. The Process according to claim 13, wherein X represents Br, OH, $OCH_3$ or an O-triflate group, and wherein a catalyst is present.

25. The method according to claim 16, wherein said disease or condition is selected from visceral pain, chronic pain, cancer pain, migraine, acute pain and neuropathic pain.

26. The method according to claim 25, wherein said disease or condition is selected from neuropathic pain, allodynia and hyperalgesia.

27. The Compound or salt according to claim 1, wherein
$R^1$ and $R^2$ are each independently selected from the group consisting of hydrogen and a linear or branched $C_{1-4}$-alkyl radical;
or
$R^1$ and $R^2$ together with the bridging nitrogen atom form a saturated or unsaturated, optionally at least mono-substituted 5- or 6-membered-heterocyclic ring;
$R^3$, $R^4$ and $R^5$ are independently from each other selected from H, F, Cl, Br, I, OH, SH, $NH_2$, $CH_3$, $C_2H_5$, $C_3H_7$, $C_4H_9$, $OCH_3$, $OC_2H_5$, $OC_3H_7$ and $OC_4H_9$;
$R^6$ and $R^7$ are independently from each other selected from H, F, Cl, Br, I, OH, SH, $NH_2$, $CH_3$, $C_2H_5$, $C_3H_7$, $C_4H_9$, $OCH_3$, $OC_2H_5$, $OC_3H_7$ and $OC_4H_9$;

$R^8$ is selected from H, F, Cl, Br, I, OH, SH, $NH_2$, $CH_3$, $C_2H_5$, $C_3H_7$, $C_4H_9$, $CH_2$—O—$CH_3$ and $CH_2$—O—$C_2H_5$; and $R^9$ and $R^{9a}$, when present, are independently from each other selected from F, Cl, Br, I, $CH_3$, $CF_3$, $C_2H_5$, $C_3H_7$, $C_4H_9$, $OCH_3$, $OC_2H_5$, $OC_3H_7$ and $OC_4H_9$.

28. Compound or salt according to claim 27, wherein $R^1$ and $R^2$ are each independently selected from the group consisting of hydrogen, $CH_3$, $C_2H_5$ and $C_3H_7$;

$R^3$, $R^4$ and $R^5$ are each H;

$R^6$ and $R^7$ are independently from each other selected from H, or $CH_3$;

$R^8$ is selected from H, $CH_3$, $C_2H_5$, $C_3H_7$, $C_4H_9$, and $CH_2$—O—$CH_3$; and $R^9$ and $R^{9a}$, when present, are independently from each other selected from F, Cl, $CH_3$, $CF_3$ and $OCH_3$.

\* \* \* \* \*

UNITED STATES PATENT AND TRADEMARK OFFICE
CERTIFICATE OF CORRECTION

PATENT NO. : 8,232,307 B2
APPLICATION NO. : 12/667587
DATED : July 31, 2012
INVENTOR(S) : Garcia-Lopez et al.

It is certified that error appears in the above-identified patent and that said Letters Patent is hereby corrected as shown below:

Column 60, Line 26: Claim 2, Delete "$R^9$ and $R^{8a}$" and insert -- $R^8$ and $R^{8a}$ --

Column 63, Line 66: Claim 10, Delete
"(R) Dimethyl-[6-(1,3,5-trimethyl-1H-pyrazol-4-yl)-indan-1-l]-amine" and insert
-- (R) Dimethyl-[6-(1,3,5-trimethyl-1H-pyrazol-4-yl)-indan-1-yl]-amine --

Column 64, Line 1: Claim 10, Delete
"(S) Dimethyl-[6-(1,3,5-trimethyl-1H-pyrazol-4-yl)-indan-1-l]-amine" and insert
-- (S) Dimethyl-[6-(1,3,5-trimethyl-1H-pyrazol-4-yl)-indan-1-yl]-amine --

Signed and Sealed this
Second Day of October, 2012

David J. Kappos
*Director of the United States Patent and Trademark Office*